(12) United States Patent
Nakashima et al.

(10) Patent No.: US 6,515,150 B2
(45) Date of Patent: Feb. 4, 2003

(54) CYCLIC ACETAL COMPOUND, POLYMER, RESIST COMPOSITION AND PATTERNING PROCESS

(75) Inventors: Mutsuo Nakashima, Nakakubiki-gun (JP); Seiichiro Tachibana, Nakakubiki-gun (JP); Takeru Watanabe, Nakakubiki-gun (JP); Takeshi Kinsho, Nakakubiki-gun (JP); Koji Hasegawa, Nakakubiki-gun (JP); Tsunehiro Nishi, Nakakubiki-gun (JP); Jun Hatakeyama, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/967,946

(22) Filed: Oct. 2, 2001

(65) Prior Publication Data

US 2002/0147290 A1 Oct. 10, 2002

(30) Foreign Application Priority Data

| Oct. 2, 2000 | (JP) | ......................... 2000-301933 |
| Jan. 18, 2001 | (JP) | ......................... 2001-010087 |
| Feb. 8, 2001 | (JP) | ......................... 2001-031720 |

(51) Int. Cl.⁷ ..................... C07D 317/26; C07D 319/06
(52) U.S. Cl. ..................... 549/454; 549/453; 549/430; 549/372
(58) Field of Search ............................... 549/454, 453, 549/430, 372

(56) References Cited

U.S. PATENT DOCUMENTS 4,861,903 A * 8/1989 Giordano et al. ........... 549/434

* cited by examiner

*Primary Examiner*—Ba K. Trinh
(74) *Attorney, Agent, or Firm*—Millen, White, Zelano & Branigan, P.C.

(57) ABSTRACT

Cyclic acetal compounds of formula (1) wherein k=0 or 1 and n is an integer of 0 to 6 are novel. Using the cyclic acetal compounds as a monomer, polymers are obtained. A resist composition comprising the polymer as a base resin is sensitive to high-energy radiation and has excellent sensitivity, resolution, and etching resistance.

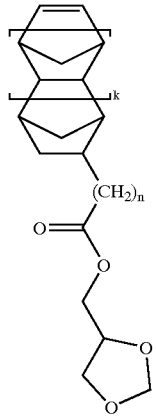

5 Claims, No Drawings

CYCLIC ACETAL COMPOUND, POLYMER, RESIST COMPOSITION AND PATTERNING PROCESS

This invention relates to (i) a novel cyclic acetal compound or a mixture of cyclic acetal compounds useful as a monomer to form a polymer, (ii) a polymer comprising specific recurring units, (iii) a resist composition comprising the polymer as a base resin, suited in a micropatterning process, and (iv) a patterning process using the resist composition.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

For resist materials for use with a KrF excimer lasers, polyhydroxystyrene having a practical level of transmittance and etching resistance is, in fact, a standard base resin. For resist materials for use with ArF excimer lasers, polyacrylic or polymethacrylic acid derivatives and polymers containing aliphatic cyclic compounds in the backbone are under investigation. All these polymers have advantages and disadvantages, and none of them have been established as the standard base resin.

More particularly, resist compositions using derivatives of polyacrylic or polymethacrylic acid have the advantages of high reactivity of acid-decomposable groups and good substrate adhesion and give relatively satisfactory results with respect to sensitivity and resolution, but have extremely low etching resistance and are impractical because the resin backbone is weak. On the other hand, resist compositions using polymers containing alicyclic compounds in their backbone have a practically acceptable level of etching resistance because the resin backbone is robust, but are very low in sensitivity and resolution because the reactivity of acid-decomposable protective groups is extremely low as compared with those on the acrylic polymers. Since the backbone of the resin is too robust, substrate adhesion is poor. These compositions are thus impractical as well. While a finer pattern rule is being demanded, there is a need to have a resist material which is satisfactory in sensitivity, resolution, and etching resistance.

SUMMARY OF THE INVENTION

Therefore, an object of the present invention is to provide (i) a novel cyclic acetal compound and a mixture of cyclic acetal compounds useful as a monomer, (ii) a polymer having improved reactivity, robustness and substrate adhesion, (iii) a resist composition comprising the polymer as a base resin, which is improved in adhesion and transparency when processed by photolithography using light having a wavelength of less than 300 nm, especially ArF excimer laser light and which has a higher resolution and etching resistance than conventional resist compositions, and (iv) a patterning process using the resist composition.

The inventors have found that novel cyclic acetal compounds of the formula (i), or mixtures of a 5-membered ring acetal compound of the formula (i) and a 6-membered ring acetal compound of the formula (v), all shown below, are easily produced in high yields by the method to be described later; that polymers obtained from the cyclic acetal compounds or the mixtures of cyclic acetal compounds are highly transparent at the exposure wavelength of an excimer laser; and that a resist composition using the polymer as a base resin is improved in adhesion to substrates. It has also been found that novel polymers comprising recurring units of the formula (1-1) or (1-2) and having a weight average molecular weight of 1,000 to 500,000, which are produced from the cyclic acetal compounds or the mixtures of cyclic acetal compounds by the method to be described later, have improved reactivity, robustness or rigidity and substrate adhesion; that a resist composition comprising the polymer as the base resin has a high resolution and etching resistance; and that this resist composition lends itself to precise micropatterning.

In a first aspect, the invention provides a cyclic acetal compound of the following general formula (i), and especially formula (ii).

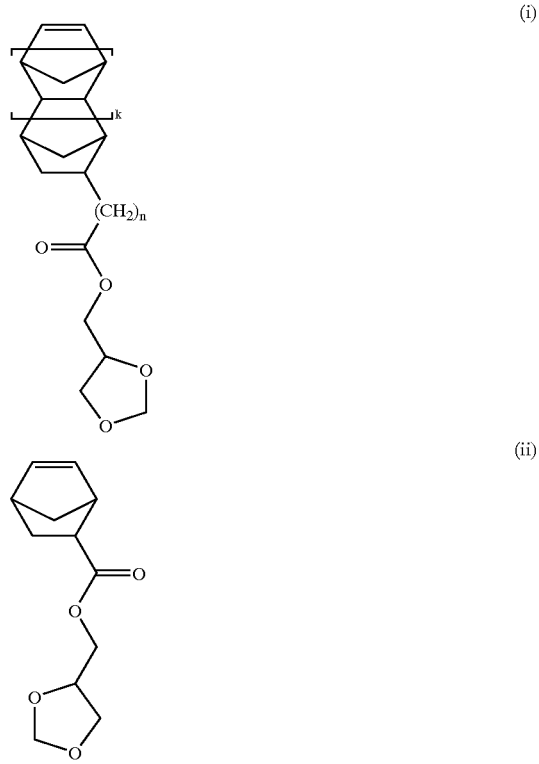

Herein k is 0 or 1 and n is an integer from 0 to 6.

The invention also provides a cyclic acetal compound mixture comprising a 5-membered ring acetal compound of the general formula (i) and a 6-membered ring acetal compound of the general formula (v), and especially a 5-membered ring acetal compound of the general formula (ii) and a 6-membered ring acetal compound of the general formula (vi).

(i)

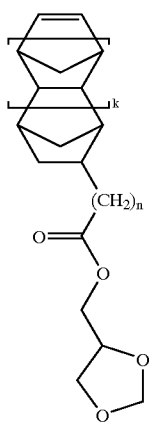

(1-1)

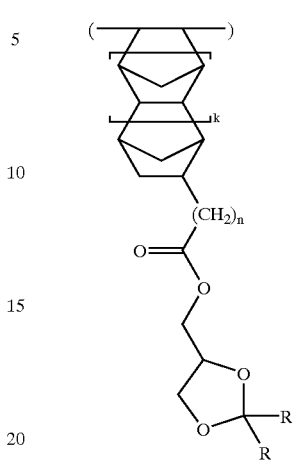

(1-1) or (1-2) and having a weight average molecular weight of 1,000 to 500,000.

(v)

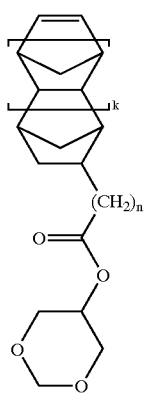

Herein k and n are defined above.

(1-2)

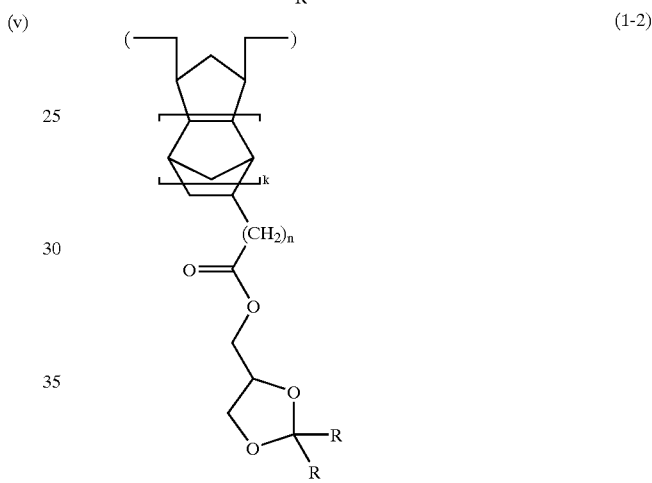

Herein R is hydrogen or methyl, k and n are as defined above.

In a preferred embodiment, the polymer further includes recurring units of the following general formula (1'-1) or (1'-2).

(ii)

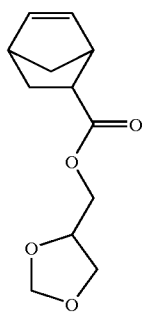

(vi)

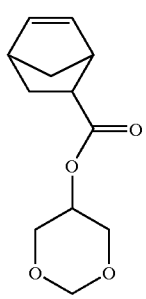

In a second aspect, the invention provides a polymer comprising recurring units of the following general formula (1'-1)

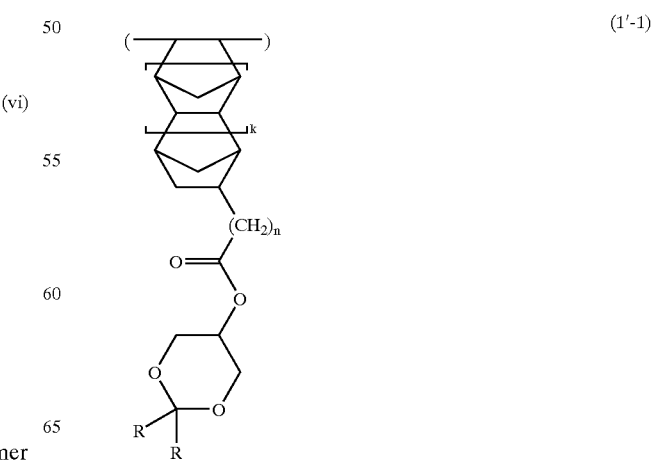

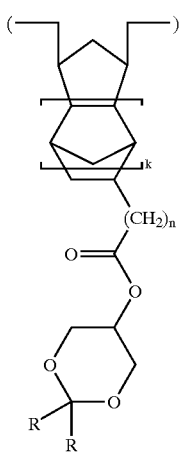 (1'-2)

Herein R, k and n are as defined above.

In another preferred embodiment, the polymer includes, in addition to the recurring units of formula (1-1), recurring units of the following general formula (2-1).

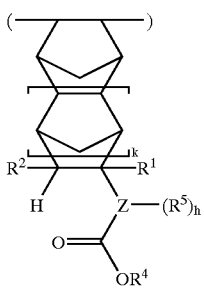 (2-1)

Herein k is as defined above; $R^1$ is hydrogen, methyl or $CH_2CO_2R^3$; $R^2$ is hydrogen, methyl or $CO_2R^3$; $R^3$ is a straight, branched or cyclic alkyl group of 1 to 15 carbon atoms; $R^4$ is an acid labile group; $R^5$ is selected from the class consisting of a halogen atom, a hydroxyl group, a straight, branched or cyclic alkoxy, acyloxy, alkoxycarbonyloxy or alkylsulfonyloxy group of 1 to 15 carbon atoms, and a straight, branched or cyclic alkoxyalkoxy group of 2 to 15 carbon atoms, in which some or all of the hydrogen atoms on constituent carbon atoms may be substituted with halogen atoms; Z is a single bond or a straight, branched or cyclic (h+2)-valent hydrocarbon group of 1 to 5 carbon atoms, in which at least one methylene may be substituted with oxygen to form a chain-like or cyclic ether or two hydrogen atoms on a common carbon may be substituted with oxygen to form a ketone; and h is 0, 1 or 2.

In a further preferred embodiment, the polymer includes, in addition to the recurring units of formula (1-1), recurring units of the following general formulae (2-1) and (3).

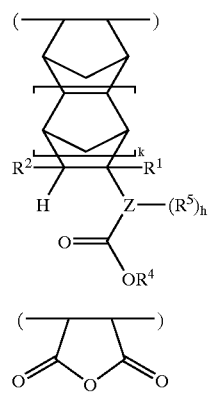 (2-1)

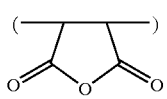 (3)

Herein k, h and $R^1$ to $R^5$ are as defined above.

In a still further preferred embodiment, the polymer includes, in addition to the recurring units of formula (1-1), recurring units of the following general formula (2-1) and/or recurring units of the following general formula (4), and recurring units of the following general formula (3).

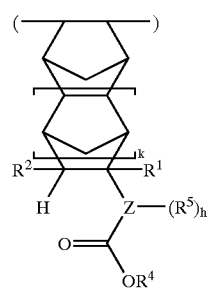 (2-1)

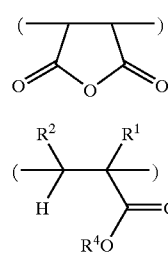 (3)

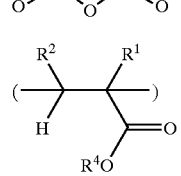 (4)

Herein k, h and $R^1$ to $R^5$ are as defined above.

The polymer of any of the preferred embodiment may further include recurring units of the general formula (11-1).

In an alternative embodiment, the polymer includes, in addition to the recurring units of formula (1-2), recurring units of the following general formula (2-2).

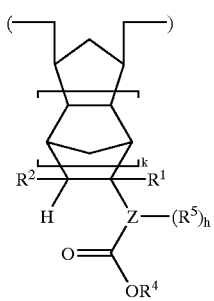

(2-2)

Herein k, h and $R^1$ to $R^5$ are as defined above. The polymer may further include recurring units of the general formula (1'-2).

In a third aspect, the invention provides a resist composition comprising the polymer defined above.

In a fourth aspect, the invention provides a process for forming a resist pattern comprising the steps of applying the resist composition onto a substrate to form a coating; heat treating the coating and then exposing it to high-energy radiation or electron beams through a photo mask; and optionally heat treating the exposed coating and developing it with a developer.

The polymers comprising recurring units of formula (1-1) or (1-2) have high rigidity since bridged aliphatic rings are incorporated in the backbone. They show improved substrate adhesion since they have on a side chain a five or six-membered ring cyclic acetal structure with a high polarity in addition to an ester structure and are thus rich in oxygen functional groups. A spacer of appropriate length introduced between the cyclic acetal structure-bearing ester portion and the rigid backbone serves to properly alleviate the rigidity which has been excessive in the prior art. Since the cyclic acetal structure moiety is spaced apart from the backbone, it can act more positively as a polar group. These factors cooperate to develop a substrate adhesion force surpassing the prior art compositions. Although low reactivity is left outstanding in the prior art, the spacer introduced allows the acid generated to diffuse smoothly, thereby improving reactivity and as an accompanying benefit, achieving a reduction of line edge roughness. Therefore, a resist composition using the polymer as a base resin satisfies all the performance factors of sensitivity, resolution and etch resistance and is very useful in forming micropatterns.

DESCRIPTION OF THE PREFERRED EMBODIMENTS

Acetal Compound

The cyclic acetal compounds of the invention has the following general formula (i):

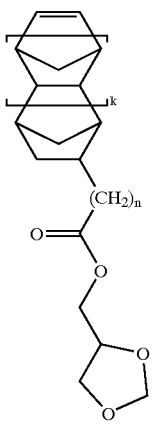

(i)

wherein k is 0 or 1 and n is an integer from 0 to 6.

Illustrative, non-limiting, examples of the cyclic acetal compounds are given below.

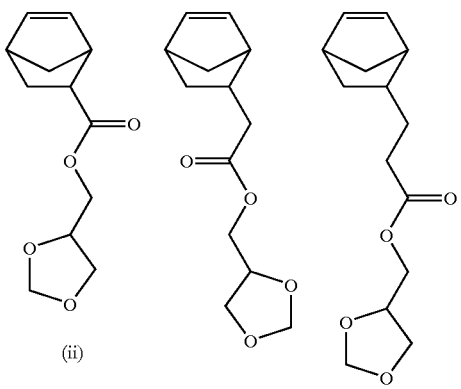

(ii)

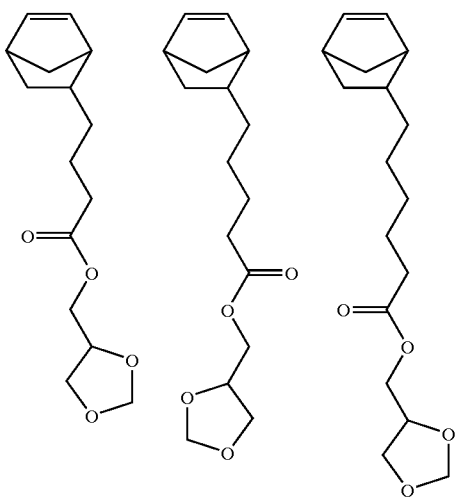

In another embodiment of the invention, a cyclic acetal compound mixture is provided comprising a 5-membered ring acetal compound of the general formula (i) and a 6-membered ring acetal compound of the general formula (v).

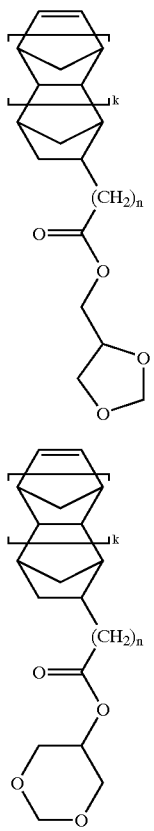

Herein k is 0 or 1 and n is an integer from 0 to 6.

Illustrative examples of the 6-membered ring acetal compound of formula (v) correspond to the above-illustrated examples of the 5-membered ring acetal compound of formula (i) in which the group (A) is replaced by the group (B) as shown below.

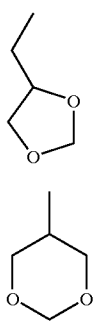

In resist polymers prepared from these compounds as monomers, the cyclic acetal moiety which is regarded to be a polar group for developing adhesion is spaced apart from the polymer backbone by a linker (represented by —$(CH_2)_n CO_2 CH_2$— in formula (i)), so that satisfactory substrate adhesion is developed. Using monomers in which k and n have optimum values, the overall polymer is properly adjusted in fat solubility and thus controlled in dissolution characteristics.

The cyclic acetal compounds or mixtures thereof according to the invention can be prepared, for example, by either of the following two methods, although the preparation method is not limited thereto.

Since glycerol formal used as the starting reactant in either of the methods contains a 5-membered ring acetal structure (iii) and an isomer, 6-membered ring acetal structure (iv), the actually obtained cyclic acetal product is a mixture of a 5-membered ring acetal compound (i) and a 6-membered ring acetal compound (v). For the sake of brevity, the following description is made on the assumption that the glycerol formal consists solely of a 5-membered ring structure (iii), that is, the 5-membered ring structure is a representative.

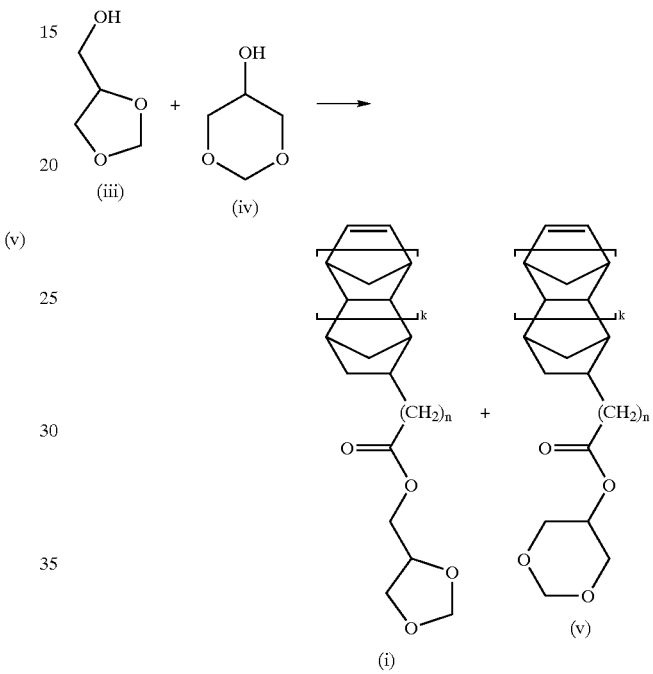

Herein k is 0 or 1 and n is an integer from 0 to 6.

In the first method, the end cyclic acetal compound (i) is synthesized by esterifying glycerol formal (iii) with an acid halide (vii) in the presence of a base.

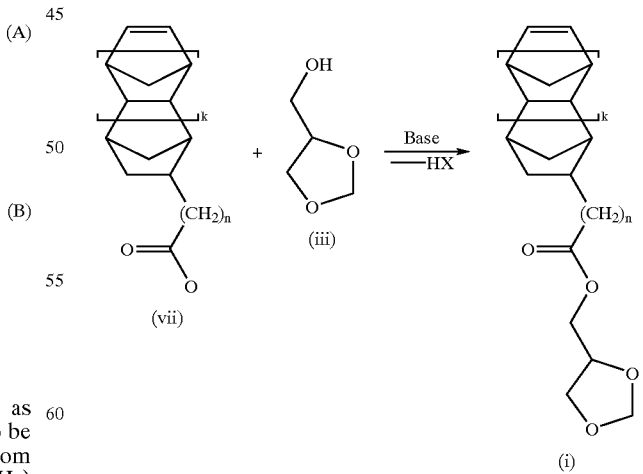

Herein X is a halogen atom, k is 0 or 1, and n is an integer from 0 to 6.

An appropriate amount of the acid halide (vii) used is 0.5 to 2.0 mol, especially 0.9 to 1.1 mol per mol of the glycerol formal (iii). The reaction is effected in the presence of a base and in a solvent or without solvent. Preferred examples of the base used herein include tertiary amines such as triethylamine, diethylisopropylamine, pyridine, N,N-dimethylaniline and 4-dimethylaminopyridine, alone or in admixture of any. The base is used in an amount of 1.0 to 20 mol. preferably 1.0 to 2.0 mol per mol of the acid halide (vii). The base itself may serve as the solvent although a suitable solvent may be used which is selected from among ethers such as tetrahydrofuran, diethyl ether, di-n-butyl ether and 1,4-dioxane, hydrocarbons such as n-hexane, n-heptane, benzene, toluene, xylene and cumene, and chlorinated solvents such as methylene chloride, chloroform and dichloroethylene. The reaction temperature is from −50° C. to 80° C., preferably 0° C. to 50° C. The reaction time is desirably determined by monitoring the reaction until the completion by gas chromatography (GC) or silica gel thin-layer chromatography (TLC) because higher yields are expectable. The reaction time is usually about 0.5 to about 20 hours. From the reaction mixture, the end cyclic acetal compound (i) is obtained by a conventional aqueous work-up step. If necessary, the end compound (i) is purified by any conventional technique such as distillation or chromatography.

In the second method, the end cyclic acetal compound (i) is synthesized from glycerol formal (iii) and an ester compound (viii).

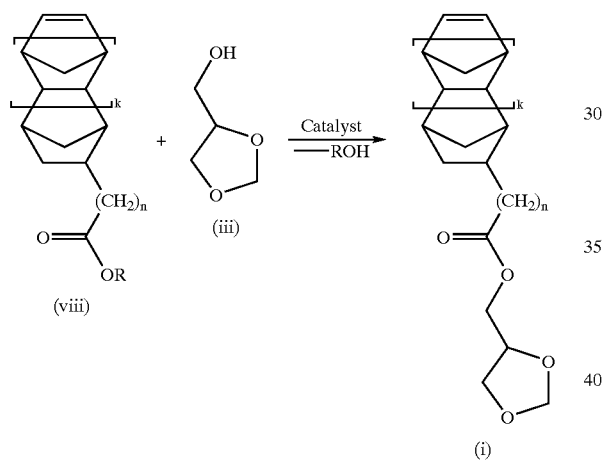

Herein R is an alkyl such as methyl or ethyl, k is 0 or 1, and n is an integer from 0 to 6.

When these reactants are used, the end compound (i) is obtained through transesterification reaction using a catalyst. The reaction may be effected in a solvent or without solvent. During the reaction, the alcohol (ROH) formed is preferably distilled off because of advantages including increased yields, reduced reaction time, and saving of the glycerol formal (iii) amount. An appropriate amount of glycerol formal (iii) used is 0.5 to 5.0 mol, especially 1.0 to 1.5 mol per mol of the ester compound (viii). The transesterification catalysts used include, though are not limited thereto, organic amines such as triethylamine, 1,8-diazabicyclo[5.4.0]-7-undecene and 4-dimethylaminopyridine, inorganic bases such as sodium hydroxide, potassium carbonate and sodium carbonate, and metal alkoxides such as sodium methoxide, potassium t-butoxide, magnesium ethoxide, and titanium (IV) methoxide. An appropriate amount of the transesterification catalyst used is 0.001 to 5.0 mol, especially 0.001 to 0.1 mol per mol of the ester compound (viii). The solvent is selected from among ethers such as tetrahydrofuran, di-n-butyl ether and 1,4-dioxane, hydrocarbons such as n-hexane, n-heptane, benzene, toluene, xylene and cumene, and chlorinated solvents such as chloroform and dichloroethylene, alone or in admixture of any. The reaction temperature is preferably from 50° C. to 200° C. though it varies with other reaction conditions. Most preferably, reaction is effected at a temperature near the boiling point of the solvent while distilling off the alcohol (ROH) formed during the reaction. The reaction time is desirably determined by monitoring the reaction until the completion by gas chromatography (GC) or silica gel thin-layer chromatography (TLC) because higher yields are expectable. The reaction time is usually about 1 to about 20 hours. From the reaction mixture, the end cyclic acetal compound (i) is obtained by a conventional aqueous work-up step. If necessary, the end compound (i) is purified by any conventional technique such as distillation or chromatography. Alternatively, the end compound (i) is isolated by direct distillation of the reaction mixture.

As described above, glycerol formal contains a 5-membered ring acetal structure (iii) and an isomer of 6-membered ring acetal structure (iv), and the actual product obtained by the above methods is a mixture of a 5-membered ring acetal compound (i) and a 6-membered ring acetal compound (v). When this monomeric mixture is used for polymerization, the resulting polymer contains units based on the 5-membered ring acetal compound (i) and exhibits the same effects as a homopolymer obtained using the 5-membered ring acetal compound (i) alone.

It is noted that the proportion of 5-membered ring acetal compound (i) and 6-membered ring acetal compound (v) in the mixture is usually between 7:3 and 3:7 and especially between 6:4 and 4:6 in molar ratio although it varies with the mixed proportion of 5-membered ring acetal compound (iii) and 6-membered ring acetal compound (iv) in the glycerol formal.

Polymer

According to the second aspect of the invention, a novel polymer is obtained using the cyclic acetal compound or cyclic acetal compound mixture described above. The polymer is defined as comprising recurring units of the following general formula (1-1) or (1-2) and having a weight average molecular weight of 1,000 to 500,000,

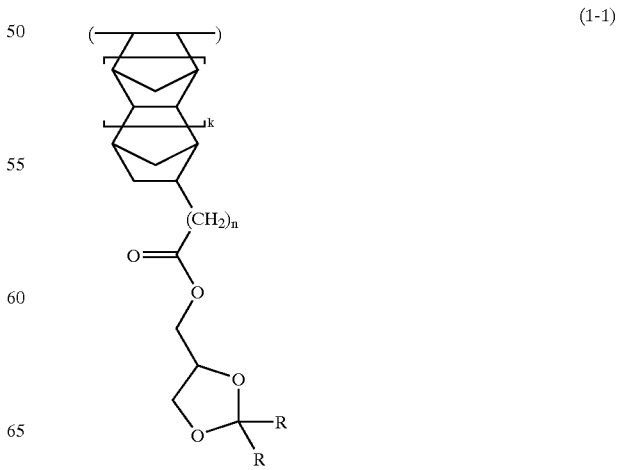

(1-1)

-continued

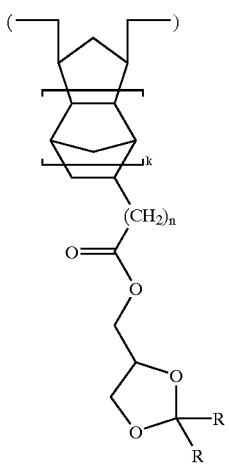
(1-2)

wherein R is hydrogen or methyl, k is 0 or 1, and n is an integer of 0 to 6.

In another embodiment, the polymer contains recurring units of the following general formula (1'-1) or (1'-2) in addition to the above units, especially in accordance with formula (1-1) or (1-2), respectively.

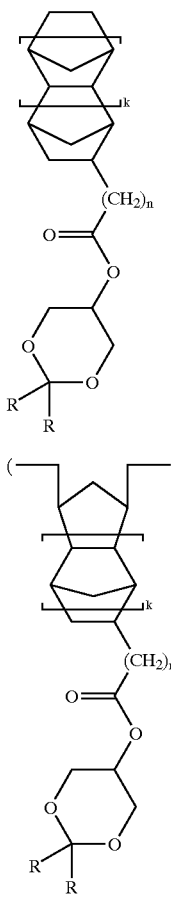

(1'-1)

(1'-2)

Herein R is hydrogen or methyl, k is 0 or 1, and n is an integer from 0 to 6.

More specifically, the polymers of the invention are divided into the following six subgenuses of polymers.

Subgenus (1) includes polymers comprising recurring units of the following general formula (2-1) as well as the recurring units of formula (1-1).

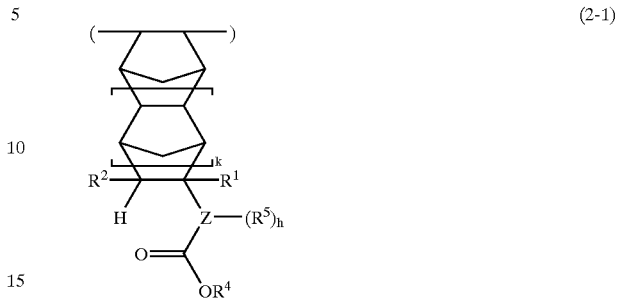
(2-1)

Herein k is as defined above, $R^1$ is hydrogen, methyl or $CH_2CO_2R^3$, $R^2$ is hydrogen, methyl or $CO_2R^3$, $R^3$ is a straight, branched or cyclic alkyl group of 1 to 15 carbon atoms, $R^4$ is an acid labile group, $R^5$ is selected from the class consisting of a halogen atom, a hydroxyl group, a straight, branched or cyclic alkoxy, acyloxy, alkoxycarbonyloxy or alkylsulfonyloxy group of 1 to 15 carbon atoms, and a straight, branched or cyclic alkoxyalkoxy group of 2 to 15 carbon atoms, in which some or all of the hydrogen atoms on constituent carbon atoms may be substituted with halogen atoms, Z is a single bond or a straight, branched or cyclic (h+2)-valent hydrocarbon group of 1 to 5 carbon atoms, in which at least one methylene may be substituted with oxygen to form a chain-like or cyclic ether or two hydrogen atoms on a common carbon may be substituted with oxygen to form a ketone, and h is 0, 1 or 2.

Subgenus (2) includes polymers comprising recurring units of the following general formulae (2-1) and (3) as well as the recurring units of formula (1-1).

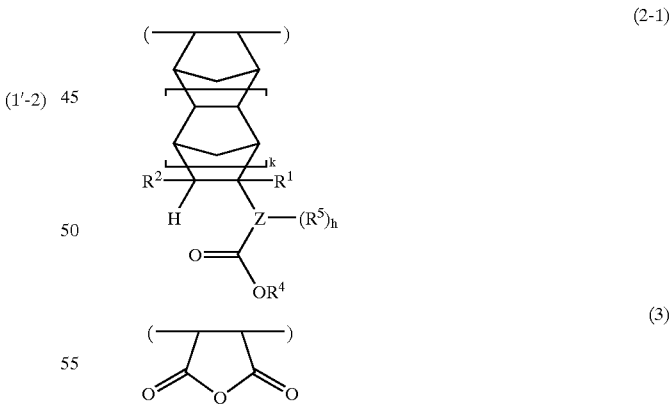

(2-1)

(3)

Herein k, h and $R^1$ to $R^5$ are as defined above.

Subgenus (3) includes polymers comprising recurring units of the following general formula (2-1) and/or recurring units of the following general formula (4), and recurring units of the following general formula (3) as well as the recurring units of formula (1-1).

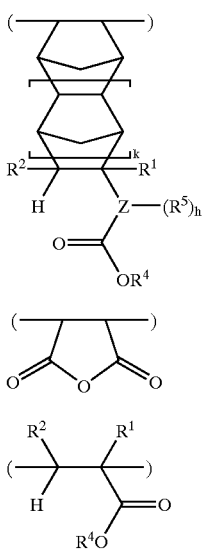
(2-1)

(3)

(4)

Herein k, h and $R^1$ to $R^5$ are as defined above.

Subgenus (4) includes polymers of subgenuses (1) to (3) further comprising recurring units of the general formula (1'-1).

Subgenus (5) includes polymers comprising recurring units of the following general formula (2-2) as well as the recurring units of formula (1-2).

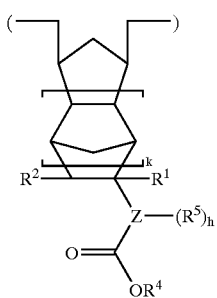
(2-2)

Herein k, h and $R^1$ to $R^5$ are as defined above.

Subgenus (6) includes polymers of subgenus (5) further comprising recurring units of the general formula (1'-2).

Herein, $R^1$ is hydrogen, methyl or $CH_2CO_2R^3$. $R^2$ is hydrogen, methyl or $CO_2R^3$. $R^3$ stands for straight, branched or cyclic alkyl groups of 1 to 15 carbon atoms, such as, for example, methyl, ethyl, n-propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl and butyladamantyl. $R^4$ stands for acid labile groups to be described later.

$R^5$ is selected from among a halogen atom, a hydroxyl group, a straight, branched or cyclic alkoxy, acyloxy, alkoxycarbonyloxy or alkylsulfonyloxy group of 1 to 15 carbon atoms, and a straight, branched or cyclic alkoxyalkoxy group of 2 to 15 carbon atoms, in which some or all of the hydrogen atoms on constituent carbon atoms may be substituted with halogen atoms. Exemplary of $R^5$ are fluoro, chloro, bromo, methoxy, ethoxy, n-propoxy, isopropoxy, n-butoxy, sec-butoxy, tert-butoxy, tert-amyloxy, n-pentoxy, n-hexyloxy, cyclopentyloxy, cyclohexyloxy, ethylcyclopentyloxy, butylcyclopentyloxy, ethylcyclohexyloxy, butylcyclohexyloxy, adamantyloxy, ethyladamantyloxy, butyladamantyloxy, formyloxy, acetoxy, ethylcarbonyloxy, pivaloyloxy, methoxycarbonyloxy, ethoxycarbonyloxy, tert-butoxycarbonyloxy, methanesulfonyloxy, ethanesulfonyloxy, n-butanesulfonyloxy, trifluoroacetoxy, trichloroacetoxy, 2,2,2-trifluoroethylcarbonyloxy, methoxymethoxy, 1-ethoxyethoxy, 1-ethoxypropoxy, 1-tert-butoxyethoxy, 1-cyclohexyloxyethoxy, 2-tetrahydrofuranyloxy, and 2-tetrahydropyranyloxy.

Z is a single bond or a straight, branched or cyclic (h+2)-valent hydrocarbon group of 1 to 5 carbon atoms, in which at least one methylene may be substituted with oxygen to form a chain-like or cyclic ether or two hydrogen atoms on a common carbon may be substituted with oxygen to form a ketone. In case of h=0, for example, exemplary Z groups are methylene, ethylene, trimethylene, tetramethylene, pentamethylene, hexamethylene, 1,2-propanediyl, 1,3-butanediyl, 1-oxo-2-oxapropane-1,3-diyl, 3-methyl-1-oxo-2-oxabutane-1,4-diyl. In case of h≠0, exemplary Z groups are (h+2)-valent groups obtained by eliminating one or two hydrogen atoms from the above-exemplified groups.

The acid labile groups represented by $R^4$ may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

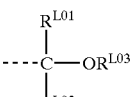
(L1)

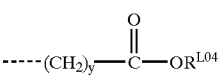
(L2)

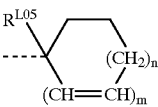
(L3)

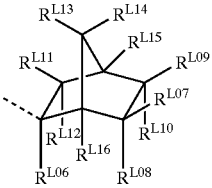
(L4)

In these formulae and throughout the specification, the broken line denotes a free valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like. Illustrative examples are the substituted alkyl groups shown below.

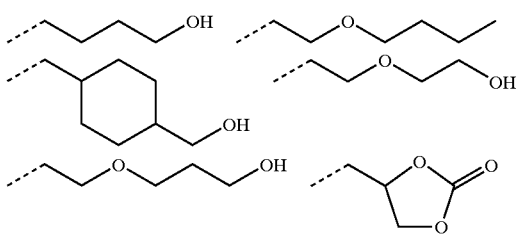

A pair of $R^{L01}$ and $R^{L02}$, $R^{L02}$ and $R^{L03}$, or $R^{L02}$ and $R^{L03}$ may form a ring. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl) propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-5-oxooxolan-4-yl. Letter y is an integer of 0 to 6.

$R^{L05}$ is a monovalent hydrocarbon group of 1 to 8 carbon atoms which may contain a hetero atom or a substituted or unsubstituted aryl group of 6 to 20 carbon atoms. Examples of the monovalent hydrocarbon group which may contain a hetero atom include straight, branched or cyclic alkyl groups such as methyl, ethyl, n-propyl, isopropyl, n-butyl, sec-butyl, tert-butyl, tert-amyl, n-pentyl, n-hexyl, cyclopentyl, and cyclohexyl, and substituted groups in which some hydrogen atoms on the foregoing groups are substituted with hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2m+n is equal to 2 or 3.

$R^{L06}$ is a monovalent hydrocarbon group of 1 to 8 carbon atoms which may contain a hetero atom or a substituted or unsubstituted aryl group of 6 to 20 carbon atoms. Examples of these groups are the same as exemplified for $R^{L05}$.

$R^{L07}$ to $R^{L16}$ independently represent hydrogen or monovalent hydrocarbon groups of 1 to 15 carbon atoms which may contain a hetero atom. Exemplary hydrocarbon groups are straight, branched or cyclic alkyl groups such as methyl, ethyl, n-propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted ones of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$–$C_{15}$ hydrocarbon group which may contain a hetero atom, when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

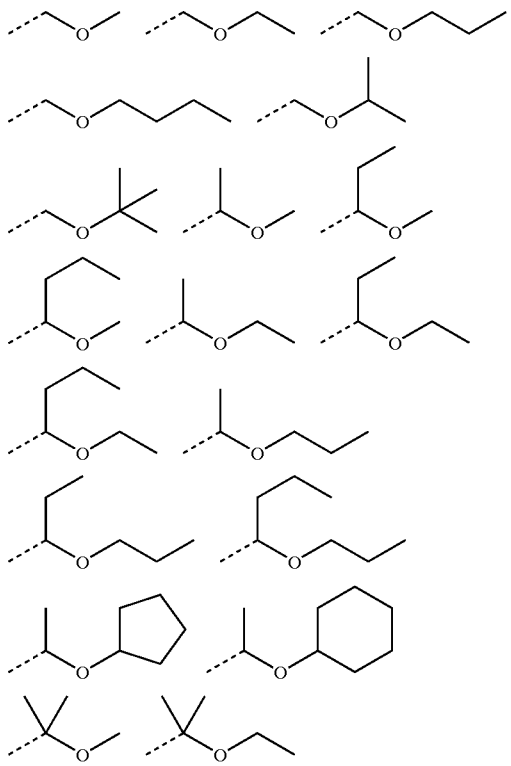

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonyl-methyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

The acid labile groups of formula (L4) are exemplified by the following groups.

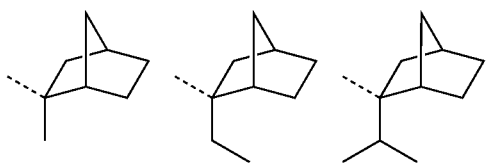

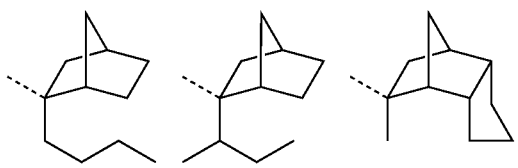

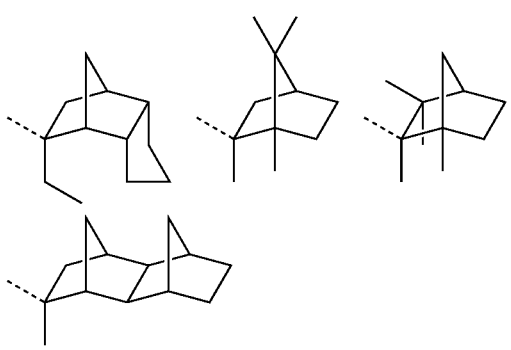

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

Illustrative, non-limiting, examples of the recurring units of formula (1-1) are given below.

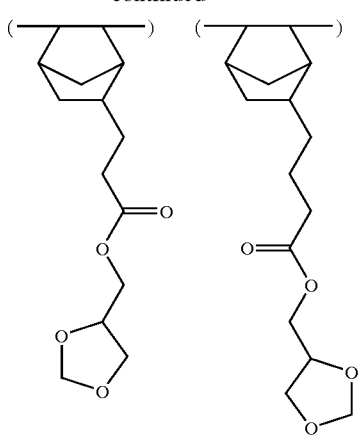

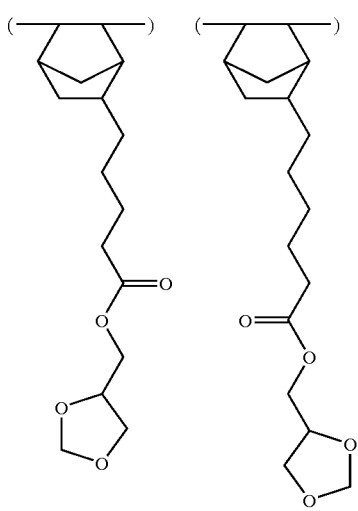

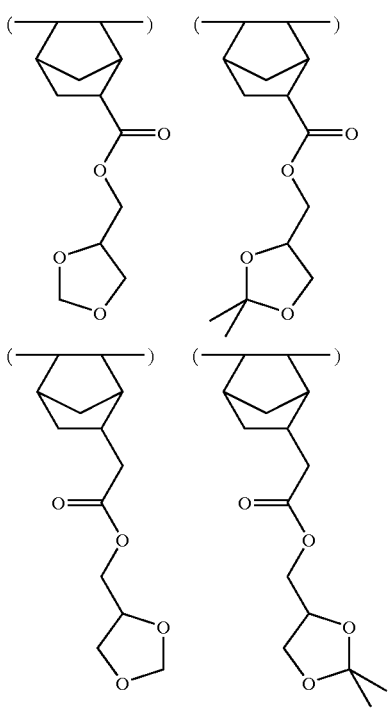

-continued

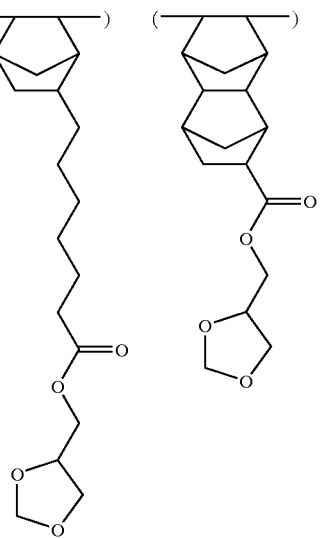

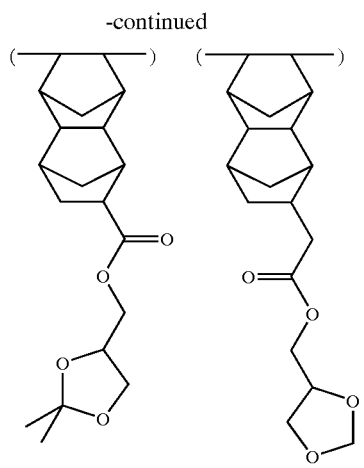
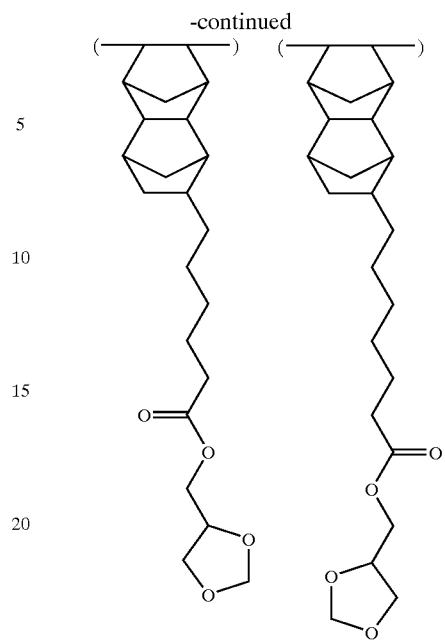
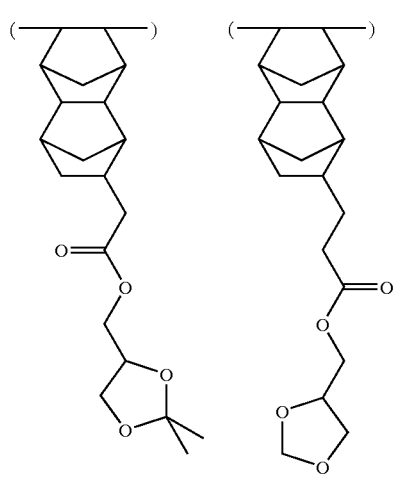
Illustrative, non-limiting, examples of the recurring units of formula (1-2) are given below.
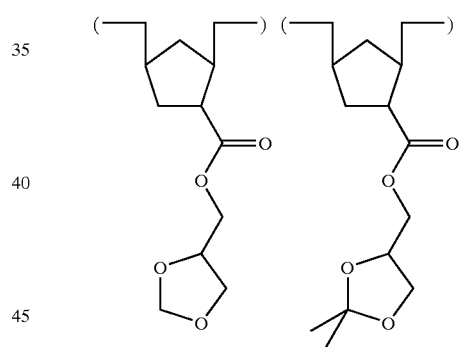
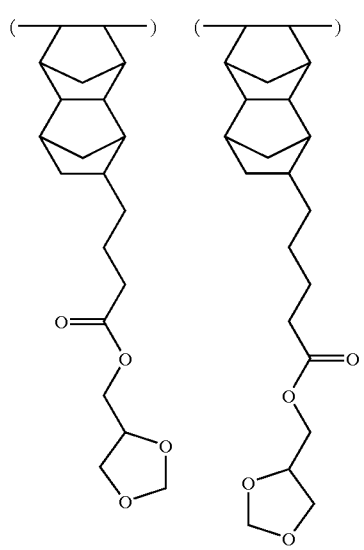
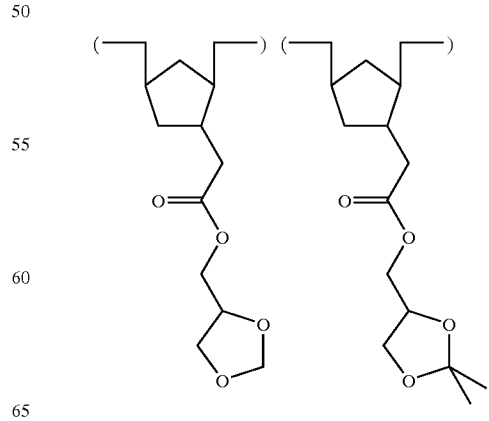

-continued
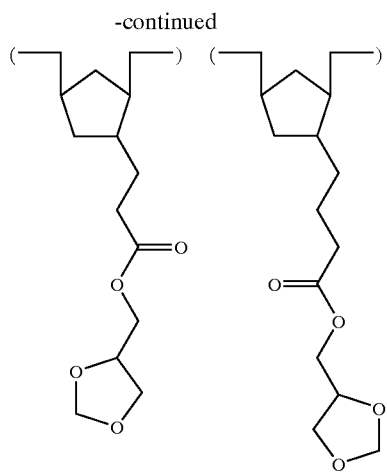
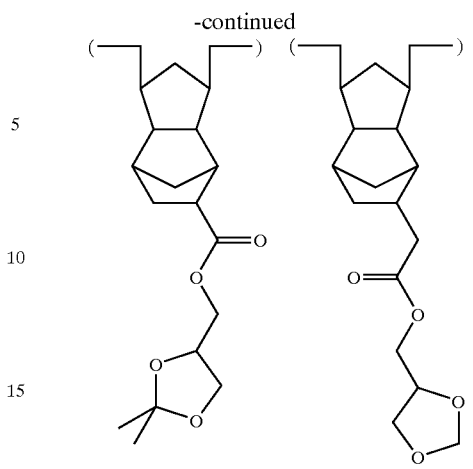
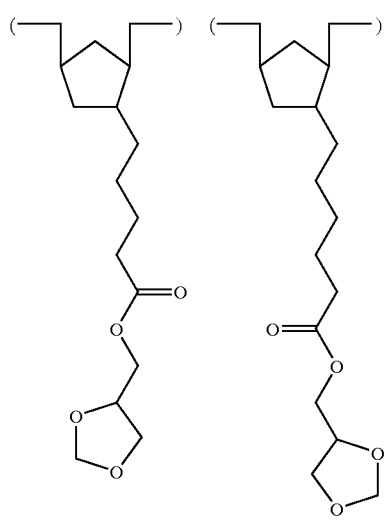
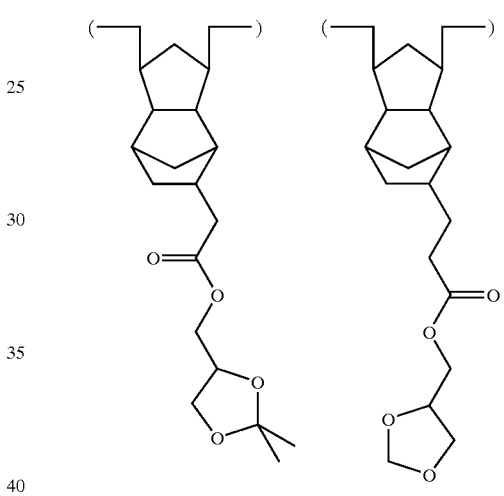
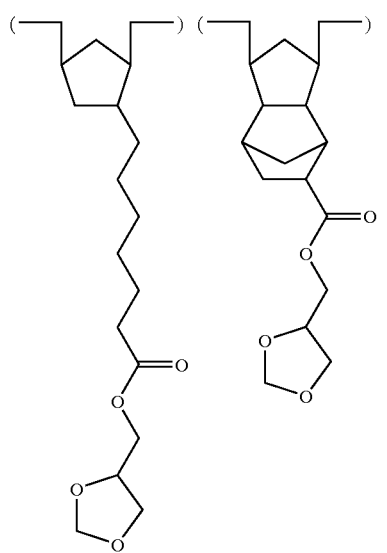
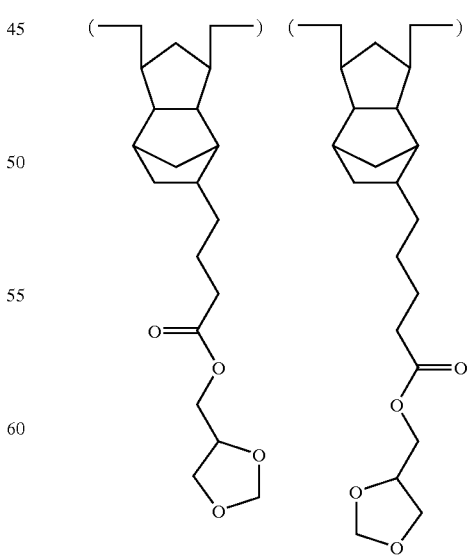

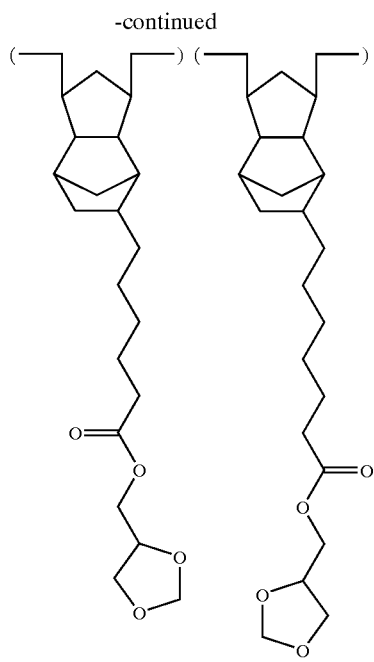
Illustrative examples of the recurring units of formula (1'-1) or (1'-2) correspond to the examples of the recurring units of formula (1-1) or (1-2), provided that the group (A) is replaced by the group (B) below.
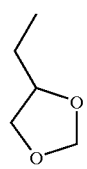
(A)
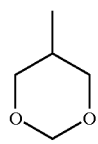
(B)
Illustrative, non-limiting, examples of the recurring units of formula (2-1) are given below.
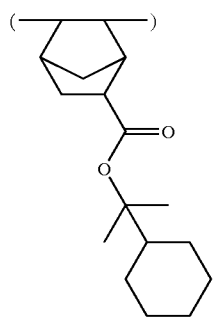
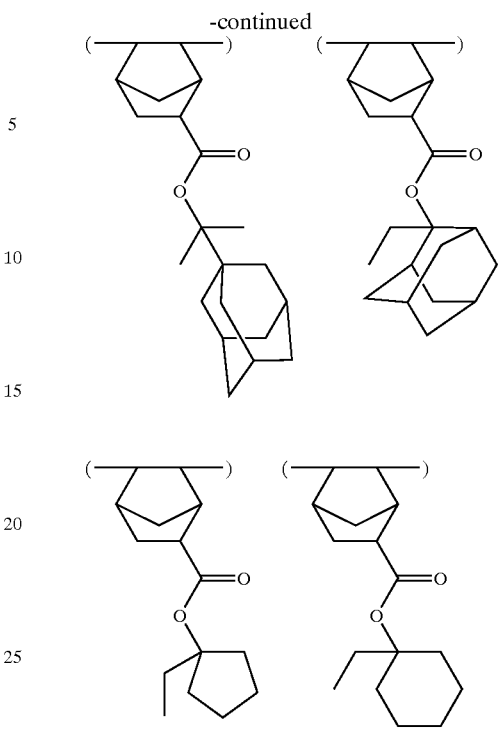
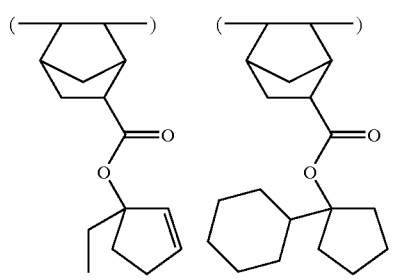
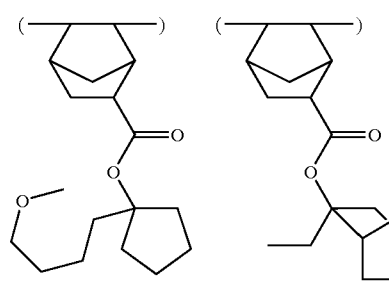
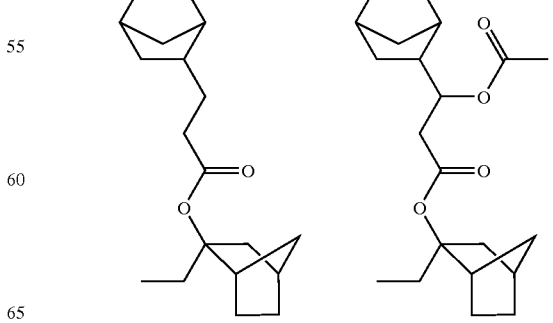

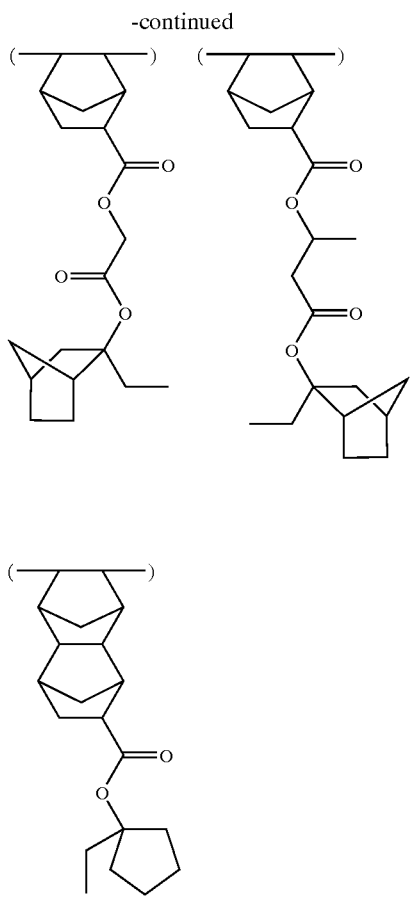
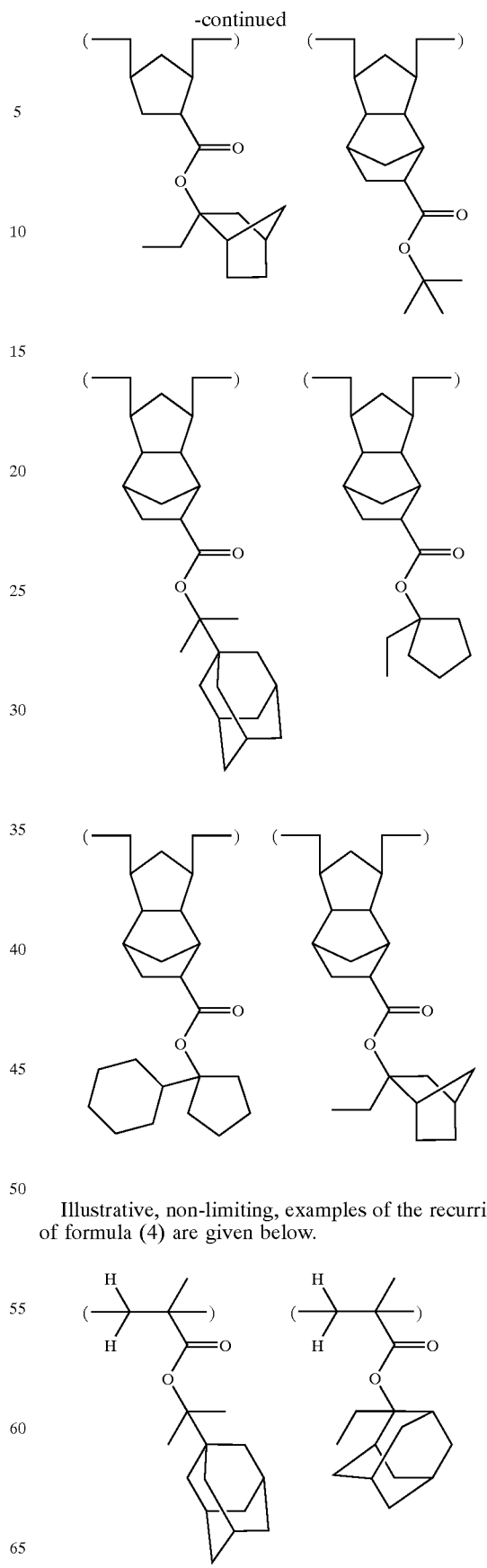
Illustrative, non-limiting, examples of the recurring units of formula (2-2) are given below.
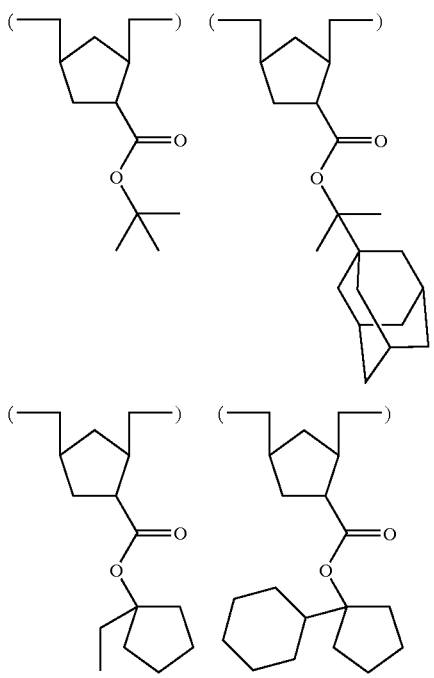
Illustrative, non-limiting, examples of the recurring units of formula (4) are given below.
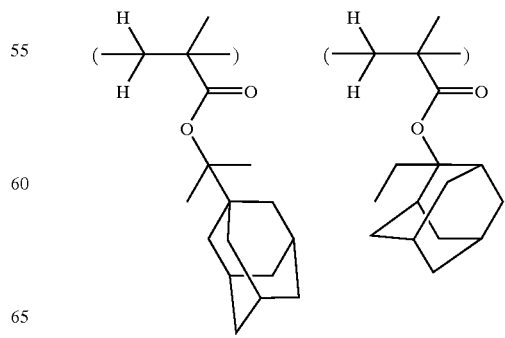

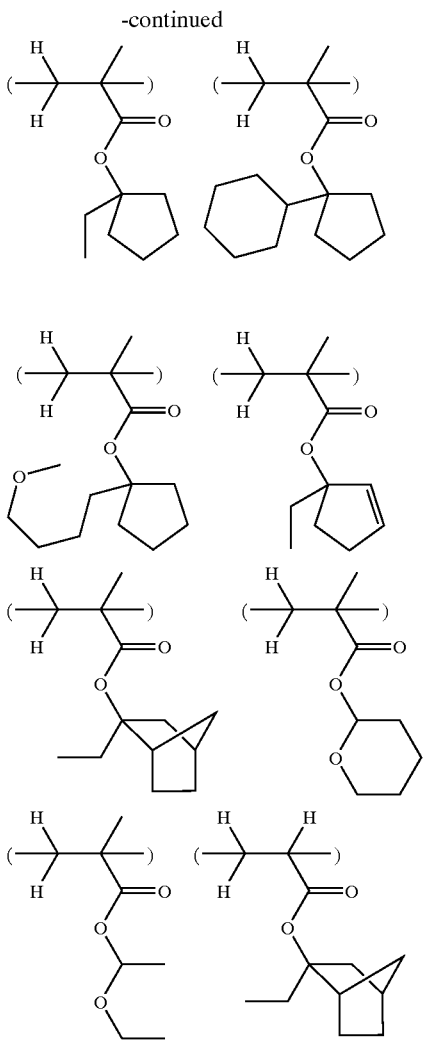
If desired, the polymers of the invention may further contain recurring units of one or more types selected from units of the following general formulae (M1) to (M8-2).
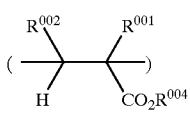 (M1)
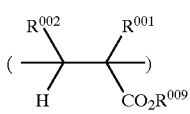 (M2)
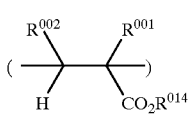 (M3)
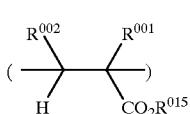 (M4)
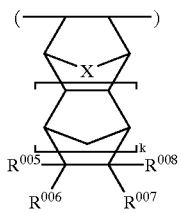 (M5-1)
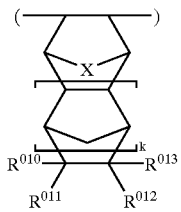 (M6-1)
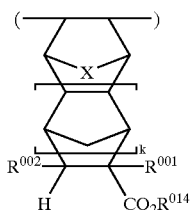 (M7-1)
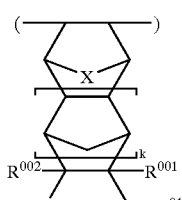 (M8-1)
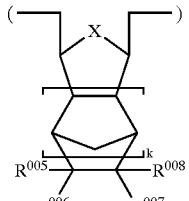 (M5-2)
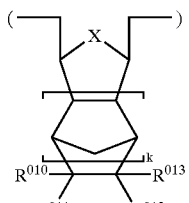 (M6-2)
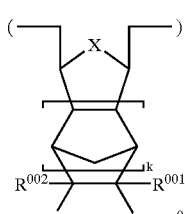 (M7-2)

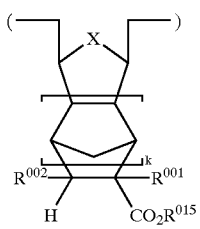

(M8-2)

Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently single bonds or straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. X is $CH_2$ or an oxygen atom. Letter k is equal to 0 or 1.

More illustratively, $R^{003}$ is a straight, branched or cyclic alkyl group of 1 to 15 carbon atoms, for example, methyl, ethyl, n-propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclo-hexyl, butylcyclohexyl, adamantyl, ethyladamantyl, and butyladamantyl.

$R^{004}$ is hydrogen or a monovalent hydrocarbon group of 1 to 15 carbon atoms having a carboxyl or hydroxyl group, for example, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxy-cyclohexyl, hydroxynorbornyl, and hydroxyadamantyl.

At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Examples of the carboxyl or hydroxyl-bearing monovalent hydrocarbon group of 1 to 15 carbon atoms include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl. Examples of the straight, branched or cyclic alkyl group of 1 to 15 carbon atoms are the same as exemplified for $R^{003}$.

Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. Examples of the carboxyl or hydroxyl-bearing divalent hydrocarbon group of 1 to 15 carbon atoms include the groups exemplified as the carboxyl or hydroxyl-bearing monovalent hydrocarbon group, with one hydrogen atom eliminated therefrom. Examples of the straight, branched or cyclic alkylene groups of 1 to 15 carbon atoms include the groups exemplified for $R^{003}$, with one hydrogen atom eliminated therefrom.

$R^{009}$ is a monovalent hydrocarbon group of 3 to 15 carbon atoms containing a —$CO_2$— partial structure, for example, 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. Examples of the monovalent hydrocarbon group of 2 to 15 carbon atoms containing a —$CO_2$— partial structure include 2-oxooxolan-3-yloxycarbonyl, 4,4-dimethyl-2-oxooxolan3-yloxycarbonyl, 4-methyl-2-oxooxan-4-yloxy-carbonyl, 2-oxo-1,3-dioxolan-4-ylmethyloxycarbonyl, and 5-methyl-2-oxooxolan-5-yloxycarbonyl. Examples of the straight, branched or cyclic alkyl groups of 1 to 15 carbon atoms are the same as exemplified for $R^{003}$.

$R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently single bonds or straight, branched or cyclic alkylene groups of 1 to 15 carbon atoms. Examples of the divalent hydrocarbon group of 1 to 15 carbon atoms containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as the groups exemplified as the monovalent hydrocarbon group containing a —$CO_2$— partial structure, with one hydrogen atom eliminated therefrom. Examples of the straight, branched or cyclic alkylene groups of 1 to 15 carbon atoms include the groups exemplified for $R^{003}$, with one hydrogen atom eliminated therefrom.

$R^{014}$ is a polycyclic hydrocarbon group having 7 to 15 carbon atoms or an alkyl group containing a polycyclic hydrocarbon group, for example, norbornyl, bicyclo[3.3.1]nonyl, tricyclo[5.2.1.0$^{2,6}$]decyl, adamantyl, ethyladamantyl, butyladamantyl, norbornylmethyl, and adamantylmethyl.

$R^{015}$ is an acid labile group, examples of which are the same as described above. X is $CH_2$ or an oxygen atom. Letter k is equal to 0 or 1.

The recurring units of formulae (M1) to (M8-2) are effective for imparting such desired properties as developer affinity, substrate adhesion and etching resistance to a resist composition based on a polymer comprising these recurring units. By adjusting the content of these recurring units, the performance of the resist composition can be finely adjusted.

The polymers of the invention have a weight average molecular weight of about 1,000 to 500,000, preferably about 3,000 to 100,000. Outside the range, the etching resistance may become extremely low and the resolution may become low because a substantial difference in rate of dissolution before and after exposure is lost.

The polymer of the invention can be prepared through copolymerization reaction using a compound of the following general formula (1a) or a mixture of a compound of formula (1a) and a compound of the following general formula (1a') as a first monomer, one, two or three members selected from compounds of the following general formulae (2a) to (4a) as second to fourth monomers, and optionally, one or more members selected from compounds of the following general formulae (M1a) to (M8a) as subsequent monomers.

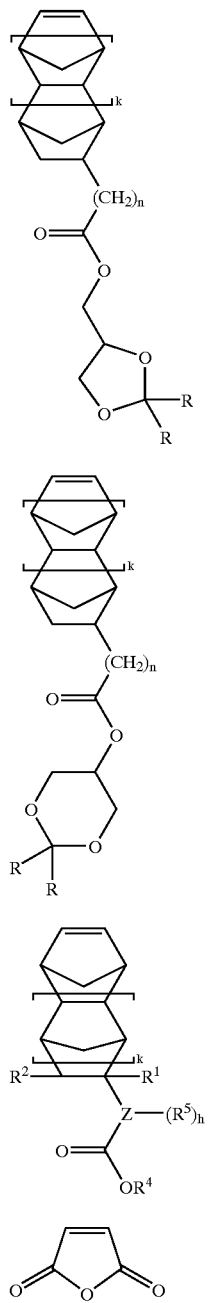

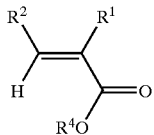

Herein, k, h, n, R, $R^1$ to $R^5$ are as defined above.

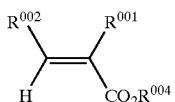

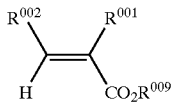

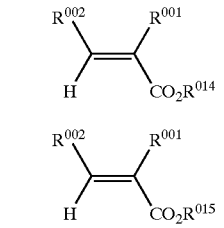

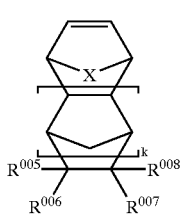

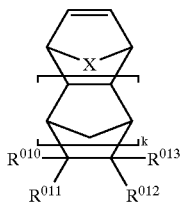

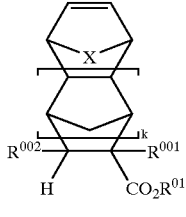

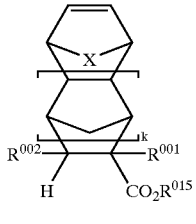

Herein, k, $R^{001}$ to $R^{015}$, and X are as defined above.

By properly adjusting the proportion of the respective monomers used in the copolymerization reaction, the polymer can be tailored so that it may exert the preferred performance when blended in resist compositions.

In addition to (i) the monomer of formula (1a) or the mixture of monomers of formulae (1a) and (1a'), (ii) the monomer or monomers of formulas (2a) to (4a), and (iii) the monomer or monomers of formulae (M1a) to (M8a), the polymer of the invention may have copolymerized therewith (iv) another monomer having a carbon-to-carbon double bond other than (i) to (iii). Examples of the additional monomer (iv) include substituted acrylic acid esters such as methyl methacrylate, methyl crotonate, dimethyl maleate, and dimethyl itaconate, unsaturated carboxylic acids such as maleic acid, fumaric acid and itaconic acid, substituted or unsubstituted norbornenes such as norbornene and methyl norbornene-5-carboxylate, and unsaturated acid anhydrides such as itaconic anhydride.

In the polymers of the invention, the preferred proportion of recurring units based on the respective monomers is in the following range, though not limited thereto.

(I) When the polymer is comprised of recurring units of formula (1-1) or formulae (1-1) and (1'-1) and recurring units of formula (2-1), it contains (i) 1 to 90%, preferably 5 to 80%, and more preferably 10 to 70% of recurring units of formula (1-1) based on the monomer of formula (1a) or recurring units of formulae (1-1) and (1'-1), (ii) 1 to 90%, preferably 5 to 80%, and more preferably 10 to 70% of recurring units of formula (2-1) based on the monomer of formula (2a), (iii) 0 to 50%, preferably 0 to 40%, and more preferably 0 to 30% of recurring units of formula (M5-1) to (M8-1) based on the monomers of formula (M5a) to (M8a), and (iv) 0 to 50%, preferably 0 to 40%, and more preferably 0 to 30% of recurring units based on another monomer.

(II) When the polymer is comprised of recurring units of formula (1-1) or formulae (1-1) and (1'-1), recurring units of formula (2-1) and recurring units of formula (3), it contains (i) 1 to 49%, preferably 3 to 45%, and more preferably 5 to 40% of recurring units of formula (1-1) based on the monomer of formula (1a) or recurring units of formulae (1-1) and (1'-1), (ii) 1 to 49%, preferably 3 to 45%, and more preferably 5 to 40% of recurring units of formula (2-1) based on the monomer of formula (2a), (iii) 50 mol % of recurring units of formula (3) based on the monomer of formula (3a), (iv) 0 to 25%, preferably 0 to 20%, and more preferably 0 to 15% of recurring units of formula (M5-1) to (M8-1) based on the monomers of formula (M5a) to (M8a), and (v) 0 to 25%, preferably 0 to 20%, and more preferably 0 to 15% of recurring units based on another monomer.

(III) When the polymer is comprised of recurring units of formula (1-1) or formulae (1-1) and (1'-1), recurring units of formula (2-1) and/or recurring units of formula (4), and recurring units of formula (3), it contains (i) 1 to 49%, preferably 3 to 45%, and more preferably 5 to 40% of recurring units of formula (1-1) based on the monomer of formula (1a) or recurring units of formulae (1-1) and (1-1), (ii) 0 to 40%, preferably 0 to 35%, and more preferably 0 to 30% of recurring units of formula (2-1) based on the monomer of formula (2a), (iii) 1 to 80%, preferably 1 to 70%, and more preferably 1 to 50% of recurring units of formula (4) based on the monomer of formula (4a), (iv) 1 to 49%, preferably 5 to 45%, and more preferably 10 to 40% of recurring units of formula (3) based on the monomer of formula (3a), (v) 0 to 25%, preferably 0 to 20%, and more preferably 0 to 15% of recurring units of formula (M1) to (M8-1) based on the monomers of formula (M1a) to (M8a), and (vi) 0 to 25%, preferably 0 to 20%, and more preferably 0 to 15% of recurring units based on another monomer.

(IV) When the polymer is comprised of recurring units of formula (1-2) or formulae (1-2) and (1'-2) and recurring units of formula (2-2), it contains (i) 1 to 90%, preferably 5 to 80%, and more preferably 10 to 70% of recurring units of formula (1-2) based on the monomer of formula (1a) or recurring units of formulae (1-2) and (1'-2), (ii) 1 to 90%, preferably 5 to 80%, and more preferably 10 to 70% of recurring units of formula (2-2) based on the monomer of formula (2a), (iii) 0 to 50%, preferably 0 to 40%, and more preferably 0 to 30% of recurring units of formula (M5-2) to (M8-2) based on the monomers of formula (M5a) to (M8a), and (iv) 0 to 50%, preferably 0 to 40%, and more preferably 0 to 30% of recurring units based on another monomer.

It is noted that where a polymer contains recurring units of formula (1-1) and recurring units of formula (1'-1), their proportion is preferably between 7:3 and 3:7, and especially between 6:4 and 4:6 in molar ratio, though not limited thereto. Also where a polymer contains recurring units of formula (1-2) and recurring units of formula (1'-2), their proportion is preferably between 7:3 and 3:7, and especially between 6:4 and 4:6 in molar ratio.

A variety of copolymerization reaction methods may be used for the preparation of the polymer according to the invention. The preferred polymerization reaction is radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base polymer of a resist composition, the third aspect of the invention provides a resist composition, especially chemically amplified resist composition, comprising the polymer. Preferably, the resist composition is defined as comprising the polymer, a photoacid generator, and an organic solvent.

Photoacid Generator

The photoacid generator is a compound capable of generating an acid upon exposure to high energy radiation or electron beams and includes the following:
(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These photoacid generators are described in detail.
(i) Onium Salts of Formula (P1a-1), (P1a-2) or (P1b)

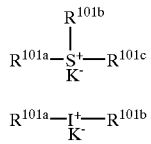

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. K⁻ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by K⁻ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

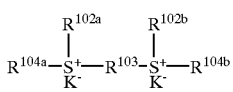

Herein, $R^{101a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. K⁻ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by K⁻ are the same as exemplified for formulae (P1a-1) and (P1a-2).

(ii) Diazomethane Derivatives of Formula (P2)

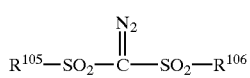

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

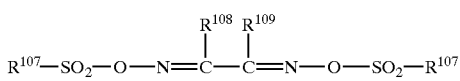

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

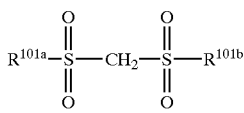

Herein, $R^{101a}$ and $R^{101b}$ are as defined above. (v) Sulfonic acid esters of N-hydroxyimide compounds of formula (P5)

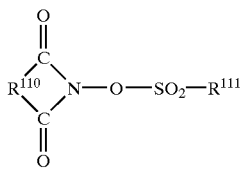

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, 1,2-ethylene, 1,3-propylene, 1,4-butylene, 1-phenyl-1,2-ethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, n-propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include:
onium salts such as diphenyliodonium trifluoromethanesulfonate, (p-tert-butoxyphenyl)phenyliodonium trifluoro-methanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis[methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl)-diazomethane, bis(p-toluenesulfonyl)diazomethane, bis-(xylenesulfonyl)diazomethane, bis(cyclohexylsulfonyl) diazo-methane, bis(cyclopentylsulfonyl)diazomethane, bis (n-butylsulfonyl)diazomethane, bis(isobutylsulfonyl) diazoethane, bis(sec-butylsulfonyl)diazomethane, bis(n-propylsulfonyl)-diazomethane, bis(isopropylsulfonyl) diazomethane, bis(tert-butylsulfonyl)diazomethane, bis(n-amylsulfonyl)diazomethane, bis(isoamylsulfonyl) diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tertamylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-

(trifluoromethanesulfonyl)-α-dimethylglyoxime, bis-O-(1,1-trifluoroethanesulfonyl)-α-dimethylglyoxime, bis-O-(tert-butanesulfonyl)-α-dimethyl-glyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris-(methanesulfonyloxy)benzene, 1,2,3-tris(trifluoromethanesulfonyloxy)benzene, and 1,2,3-tris(p-toluenesulfonyloxy)-benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)-diazomethane, bis(cyclohexylsulfonyl)diazomethane, bis(n-butylsulfonyl)diazomethane, bis(isobutylsulfonyl)diazo-methane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-O-(p-toluenesulfonyl)-α-dimethylglyoxime and bis-O-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 15 parts, and especially 0.5 to 8 parts by weight, per 100 parts by weight of the base resin (all parts are by weight, hereinafter). Less than 0.1 part of the photoacid generator would provide a poor sensitivity whereas more than parts of the photoacid generator would adversely affect transparency and resolution.

Organic Solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether and 1-ethoxy-2-propanol because the photoacid generator is most soluble therein, propylene glycol monomethyl ether acetate because it is a safe solvent, or a mixture thereof.

An appropriate amount of the organic solvent used is about 200 to 1,000 parts, especially about 400 to 800 parts by weight per 100 parts by weight of the base resin.

Other Polymer

To the resist composition of the invention, another polymer other than the inventive polymer comprising recurring units of formula (1-1) or (1-2) may also be added. The other polymers that can be added to the resist composition are, for example, those polymers comprising units of the following formula (R1) and/or (R2) and having a weight average molecular weight of about 1,000 to about 500,000, especially about 5,000 to about 100,000 although the other polymers are not limited thereto.

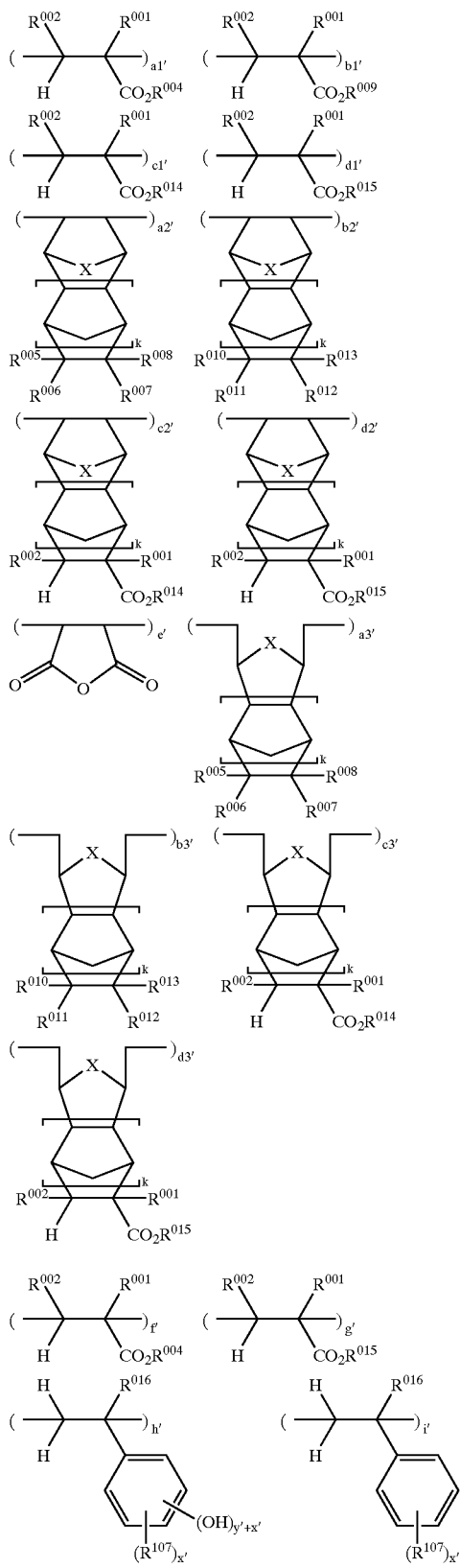

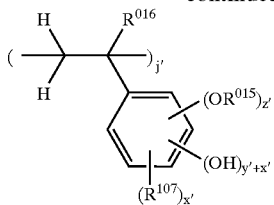

Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently single bonds or straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. $R^{016}$ is hydrogen or methyl. $R^{017}$ is a straight, branched or cyclic alkyl group of 1 to 8 carbon atoms. X is $CH_2$ or an oxygen atom. Letter k' is equal to 0 or 1; a1', a2', a3', b1', b2', b3', c1', c2', c3', d1', d2', d3', and e' are numbers from 0 to less than 1, satisfying a1'+a2'+a3'+b1'+b2'+b3'+c1'+c2'+c3'+d1'+d2'+d3'+e'=1; f', g', h', i', and j' are numbers from 0 to less than 1, satisfying f'+g'+h'+i'+j'=1.

Exemplary groups of these R's are as exemplified above.

The inventive polymer (comprising recurring units of formula (1-1) or (1-2)) and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Dissolution Regulator

To the resist composition, a dissolution regulator may be added. The dissolution regulator is a compound having on the molecule at least two phenolic hydroxyl groups, in which an average of from 0 to 100 molt of all the hydrogen atoms on the phenolic hydroxyl groups are replaced with acid labile groups or a compound having on the molecule at least one carboxyl group, in which an average of 50 to 100 molt of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid labile groups is on average at least 50 mol %, and preferably at least 70 mol %, of all the carboxyl groups, with the upper limit being 100 mol %.

Preferable examples of such compounds having two or more phenolic hydroxyl groups or compounds having at least one carboxyl group include those of formulas (D1) to (D14) below.

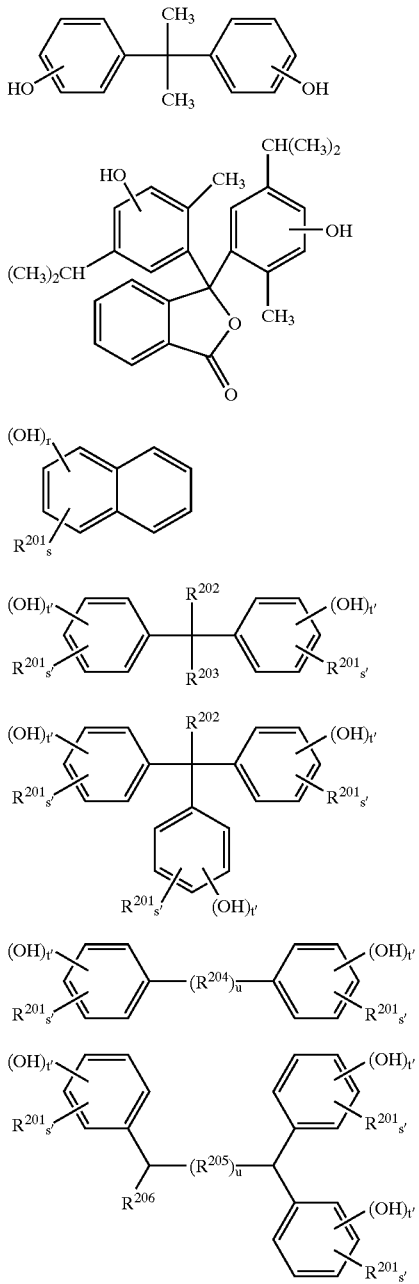

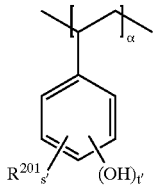

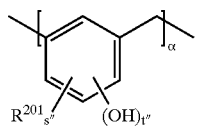

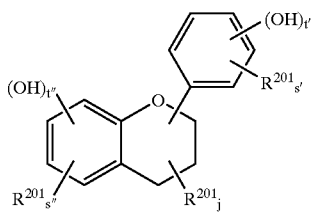

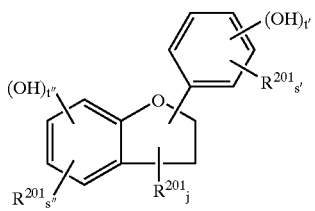

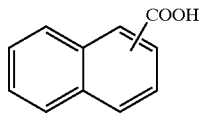

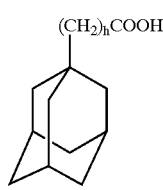

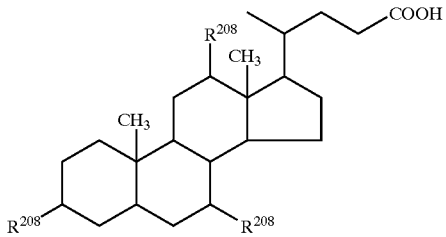

In these formulas, $R^{201}$ and $R^{202}$ are each hydrogen or a straight or branched alkyl or alkenyl of 1 to 8 carbon atoms; $R^{203}$ is hydrogen, a straight or branched alkyl or alkenyl of 1 to 8 carbon atoms, or —$(R^{207})_h$—COOH; $R^{204}$ is —$(CH_2)_i$— (where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter j is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and α is a number such that the compounds of formula (D8) or (D9) have a molecular weight of from 100 to 1,000.

In the above formulas, suitable examples of $R^{201}$ and $R^{202}$ include hydrogen, methyl, ethyl, propyl, butyl, ethynyl, and cyclohexyl; suitable examples of $R^{203}$ include the same groups as for $R^{201}$ and $R^{202}$, as well as —COOH and —CH$_2$COOH; suitable examples of $R^{204}$ include ethylene, phenylene, carbonyl, sulfonyl, oxygen, and sulfur; suitable examples of $R^{205}$ include methylene as well as the same groups as for $R^{204}$; and suitable examples of $R^{206}$ include hydrogen, methyl, ethyl, propyl, butyl, ethynyl, cyclohexyl, and hydroxyl-substituted phenyl or naphthyl.

Exemplary acid labile groups on the dissolution regulator include groups of the following general formulae (L1) to (L4), tertiary alkyl groups of 4 to 20 carbon atoms, trialkylsilyl groups in which each of the alkyls has 1 to 6 carbon atoms, and oxoalkyl groups of 4 to 20 carbon atoms.

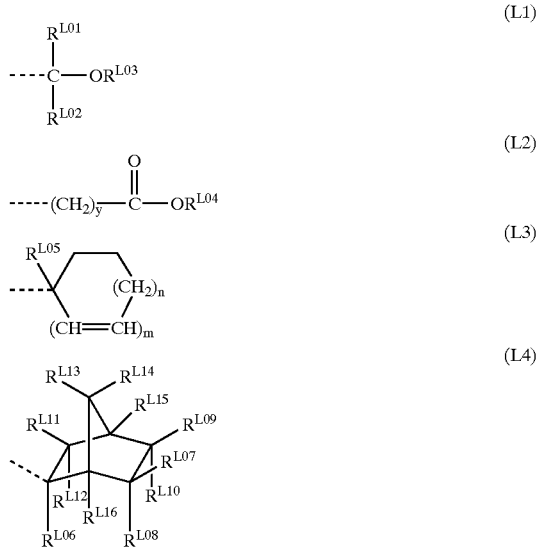

In these formulas, $R^{L01}$ and $R^{L02}$ are each hydrogen or a straight, branched or cyclic alkyl having 1 to 18 carbon atoms; and $R^{L03}$ is a monovalent hydrocarbon group of 1 to 18 carbon atoms which may contain a heteroatom (e.g., oxygen). A pair of $R^{L01}$ and $R^{L02}$, a pair of $R^{L01}$ and $R^{L03}$, or a pair of $R^{L02}$ and $R^{L03}$ may together form a ring, with the proviso that $R^{L01}$, $R^{L02}$, and $R^{L03}$ are each a straight or branched alkylene of 1 to 18 carbon atoms when they form a ring. $R^{L04}$ is a tertiary alkyl group of 4 to 20 carbon atoms, a trialkysilyl group in which each of the alkyls has 1 to 6 carbon atoms, an oxoalkyl group of 4 to 20 carbon atoms, or a group of the formula (L1). $R^{L05}$ is a monovalent hydrocarbon groups of 1 to 8 carbon atoms which may contain a hetero atom or a substituted or unsubstituted aryl group of 6 to 20 carbon atoms. $R^{L06}$ is a monovalent hydrocarbon groups of 1 to 8 carbon atoms which may contain a hetero atom or a substituted or unsubstituted aryl group of 6 to 20 carbon atoms. $R^{L07}$ to $R^{L16}$ independently represent hydrogen or monovalent hydrocarbon groups of 1 to 15 carbon atoms which may contain a hetero atom. Alternatively, $R^{L07}$ to $R^{L16}$, taken together, may form a ring. Each of $R^{L07}$ to $R^{L16}$ represents a divalent $C_1$–$C_{15}$ hydrocarbon group which may contain a hetero atom, when they form a ring. Two of $R^{L07}$ to $R^{L16}$ which are attached to adjoining carbon atoms may bond together directly to form a double bond. Letter y is an integer of 0 to 6. Letter m is equal to 0 or 1, n is equal to 0, 1, 2 or 3, and 2m+n is equal to 2 or 3. Illustrative examples of these groups are as previously exemplified.

The dissolution regulator may be formulated in an amount of 0 to 50 parts, preferably 0 to 40 parts, and more preferably 0 to 30 parts, per 100 parts of the base resin, and may be used singly or as a mixture of two or more thereof. The use of more than 50 parts would lead to slimming of the patterned film, and thus a decline in resolution.

The dissolution regulator can be synthesized by introducing acid labile groups into a compound having phenolic hydroxyl or carboxyl groups in accordance with an organic chemical formulation.

Basic Compound

In the resist composition of the invention, a basic compound may be blended. A suitable basic compound used herein is a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-isopropylamine, di-n-butylamine, di-iso-butylamine, di-secbutylamine, dipentylamine, dicyclopentylamine, dihexylamine, dicyclohexylamine, diheptylamine, dioctylamine, dinonylamine, didecylamine, didodecylamine, dicetylamine, N,N-dimethyl-methylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N- dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butyl-pyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethyl-propyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinoline-carbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-amino-pyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanol-amine, triisopropanolamine, 2,2'-iminodiethanol, 2-amino-ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]-piperazine, piperidine ethanol, 1-(2-hydroxyethyl)-pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxy-ethyl)phthalimide, and N-(2-hydroxyethyl)isonicotinamide. Examples of suitable amide derivatives include formamide, N-methylformamide, N,N-dimethylformamide, acetamide, N-methyl-acetamide, N,N-dimethylacetamide, propionamide, and benzamide. Suitable imide derivatives include phthalimide, succinimide, and maleimide.

In addition, basic compounds of the following general formula (B1) may also be included alone or in admixture.

$$N(X)_n(Y)_{3-n} \tag{B1}$$

In the formula, n is equal to 1, 2 or 3; side chain Y is independently hydrogen or a straight, branched or cyclic alkyl group of 1 to 20 carbon atoms which may contain a hydroxyl group or ether; and side chain X is independently selected from groups of the following general formulas (X1) to (X3), and two or three X's may bond together to form a ring.

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl group, ether, ester or lactone ring; $R^{303}$ is a single bond or a straight or branched alkylene group of 1 to 4 carbon atoms; and $R^{306}$ is a single bond or a straight, branched or cyclic alkyl group of 1 to 20 carbon atoms which may contain one or more hydroxyl groups, ether groups, ester groups or lactone rings.

Illustrative examples of the compounds of formula (B1) include tris(2-methoxymethoxyethyl)amine, tris{2-(methoxyethoxy)ethyl}-amine, tris{2-(2-methoxyethoxymethoxy)ethyl}-amine, tris(2-(1-methoxyethoxy)ethyl)amine, tris(2-(1-ethoxyethoxy)ethyl)}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)-amine, tris(2-pivaloyloxyethyl)amine, N,N-bis(2-acetoxy-ethyl)-2-(acetoxyacetoxy)ethylamine, tris(2-methoxycarbonyl-oxyethyl)amine, tris(2-tert-butoxycarbonyloxyethyl)amine, tris[2-(2-oxopropoxy)ethyl]amine, tris[2-(methoxycarbonyl-methyl)oxyethyl] amine, tris[2-(tert-butoxycarbonylmethyl-oxy)ethyl]amine, tris[2-(cyclohexyloxycarbonylmethyloxy)-ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxy-ethyl)-2-(2-hydroxyethoxycarbonyl) ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)-methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl) ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl) ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)

oxycarbonyl]ethylamine, N,N-bis(2-hydroxy-ethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)-ethylamine, N,N-bis(2-methoxyethyl)-2-(methoxycarbonyl)-ethylamine, N-(2-hydroxyethyl)-bis[2-(methoxycarbonyl)-ethyl]amine, N-(2-acetoxyethyl)-bis[2-(methoxycarbonyl)-ethyl]amine, N-(2-hydroxyethyl)-bis[2-(ethoxycarbonyl)-ethyl]amine, N-(2-acetoxyethyl)-bis[2-(ethoxycarbonyl)-ethyl]amine, N-(3-hydroxy-1-propyl)-bis[2-(methoxycarbonyl)-ethyl]amine, N-(3-acetoxy-1-propyl)-bis[2-(methoxycarbonyl)-ethyl]amine, N-(2-methoxyethyl)-bis[2-(methoxycarbonyl)-ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxy-carbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)-amine, and β-(diethylamino)-δ-valerolactone.

The basic compound is preferably formulated in an amount of 0.001 to 10 parts, and especially 0.01 to 1 part, per part of the photoacid generator. Less than 0.001 part of the basic compound may fail to achieve the desired effects thereof, while the use of more than 10 parts would result in too low a sensitivity and resolution.

Other Components

In the resist composition, a compound bearing a ≡C—COOH group in a molecule may be blended. Exemplary, non-limiting compounds bearing a ≡C—COOH group include one or more compounds selected from Groups I and II below. Including this compound improves the PED stability of the resist and ameliorates edge roughness on nitride film substrates.

Group I

Compounds in which some or all of the hydrogen atoms on the phenolic hydroxyl groups of the compounds of general formulas (A1) to (A10) below have been replaced with —R$^{401}$—COOH (wherein R$^{401}$ is a straight or branched alkylene of 1 to carbon atoms), and in which the molar ratio C/(C+D) of phenolic hydroxyl groups (C) to ≡C—COOH groups (D) in the molecule is from 0.1 to 1.0.

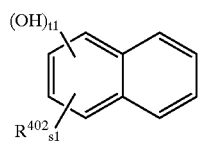
A1

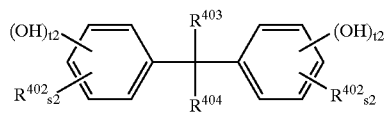
A2

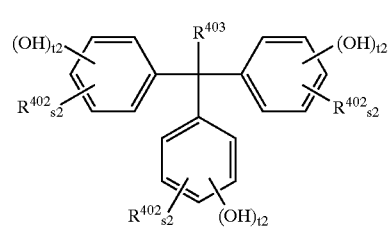
A3

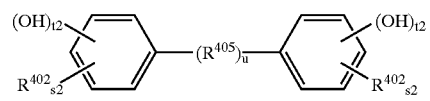
A4

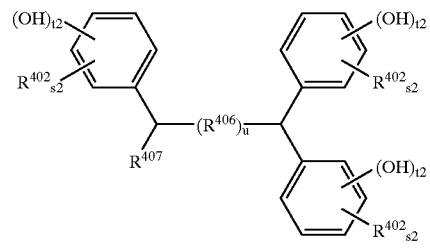
A5

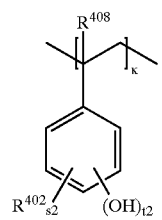
A6

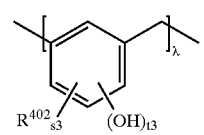
A7

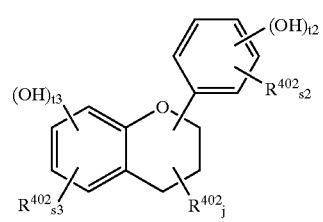
A8

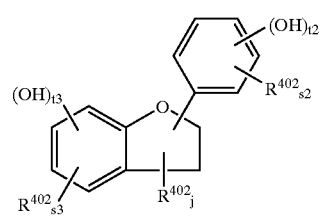
A9

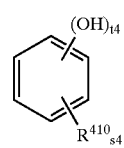
A10

In these formulas, R$^{408}$ is hydrogen or methyl; R$^{402}$ and R$^{403}$ are each hydrogen or a straight or branched alkyl or alkenyl of 1 to 8 carbon atoms; R$^{404}$ is hydrogen, a straight or branched alkyl or alkenyl of 1 to 8 carbon atoms, or a —(R$^{409}$)$_h$—COOR' group (R' being hydrogen or —R$^{409}$—

COOH); $R^{405}$ is —$(CH_2)_i$— (wherein i is 2 to 10), an arylene of 6 to 10 carbon atoms, carbonyl, sulfonyl, an oxygen atom, or a sulfur atom; $R^{406}$ is an alkylene of 1 to 10 carbon atoms, an arylene of 6 to 10 carbon atoms, carbonyl, sulfonyl, an oxygen atom, or a sulfur atom; $R^{407}$ is hydrogen, a straight or branched alkyl or alkenyl of 1 to 8 carbon atoms, or a hydroxyl-substituted phenyl or naphthyl; $R^{409}$ is a straight or branched alkylene of 1 to 10 carbon atoms; $R^{410}$ is hydrogen, a straight or branched alkyl or alkenyl of 1 to 8 carbon atoms, or a —$R^{411}$—COOH group; $R^{411}$ is a straight or branched alkylene of 1 to carbon atoms; the letter j is an integer from 0 to 5; u and h are each 0 or 1; s1, t1, s2, t2, s3, t3, s4, and t4 are each numbers which satisfy s1+t1=8, s2+t2=5, s3+t3=4, and s4+t4=6, and are such that each phenyl skeleton has at least one hydroxyl group; κ is a number such that the compound of formula (A6) may have a weight average molecular weight of 1,000 to 5,000; and λ is a number such that the compound of formula (A7) may have a weight average molecular weight of 1,000 to 10,000.

Group II

Compounds of general formulas (A11) to (A15) below.

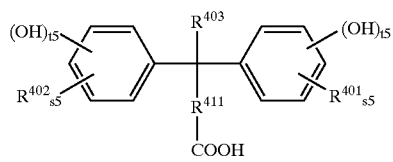

A11

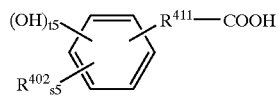

A12

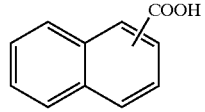

A13

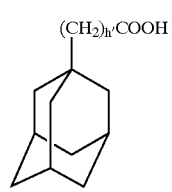

A14

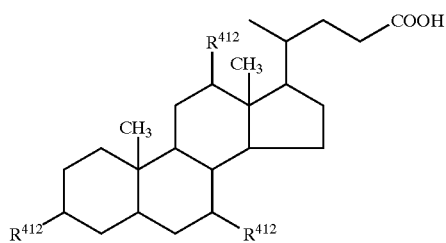

A15

In these formulas, $R^{402}$, $R^{403}$, and $R^{411}$ are as defined above; $R^{412}$ is hydrogen or hydroxyl; s5 and t5 are numbers which satisfy s5≧0, t5≧0, and s5+t5=5; and h' is equal to 0 or 1.

Illustrative, non-limiting examples of the compound bearing a ≡C—COOH group include compounds of the general formulas AI-1 to AI-14 and AII-1 to AII-10 below.

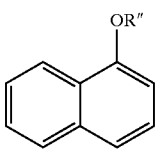

AI-1

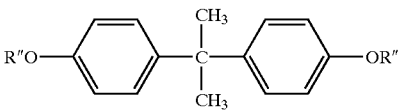

AI-2

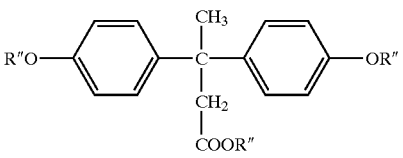

AI-3

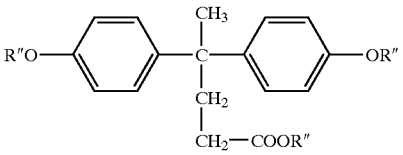

AI-4

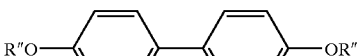

AI-5

AI-6

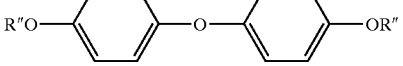

AI-7

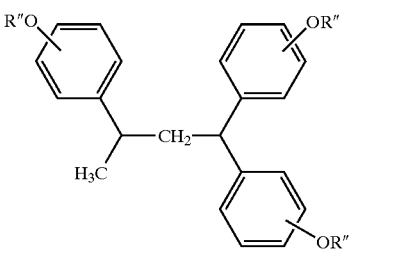

AI-8

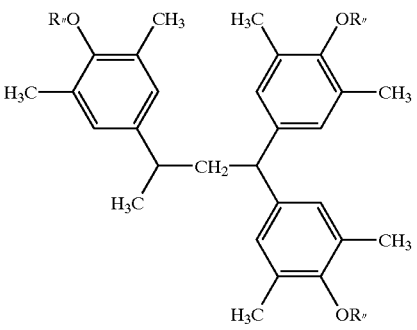

AI-9

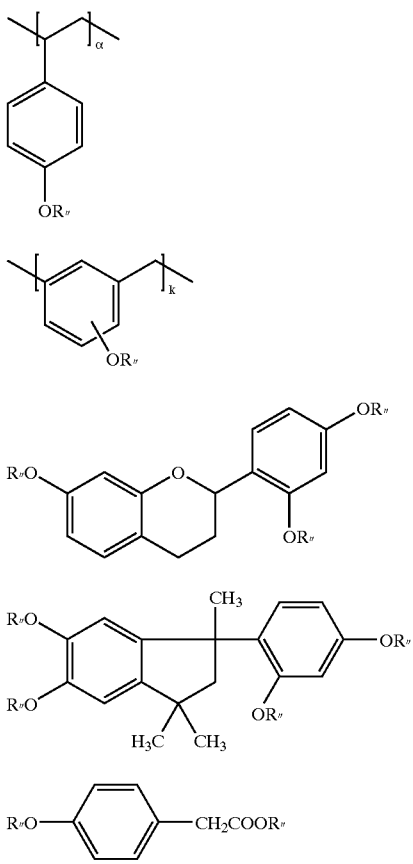

In the above formulas, R″ is hydrogen or a CH₂COOH group such that the CH₂COOH group accounts for 10 to 100 mol % of R″ in each compound, α and κ are as defined above.

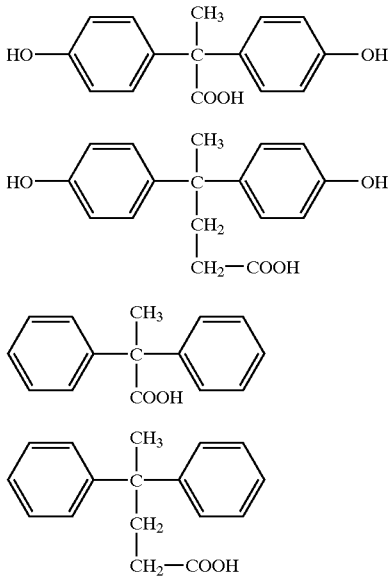

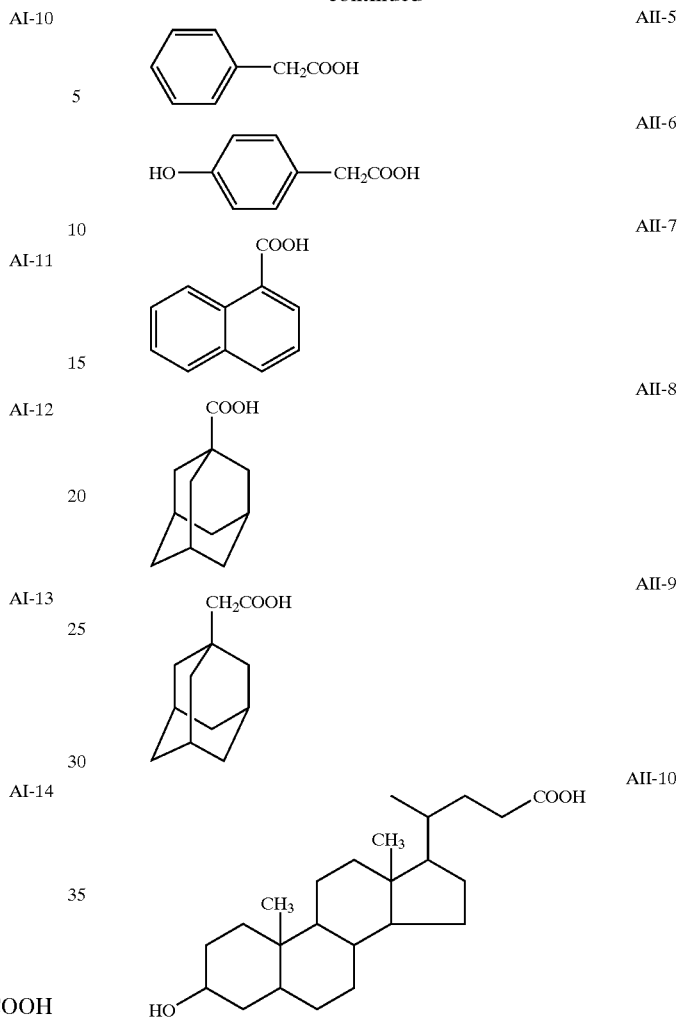

The compound bearing a ≡C—COOH group within the molecule may be used singly or as combinations of two or more thereof.

The compound bearing a ≡C—COOH group within the molecule is added in an amount ranging from 0 to 5 parts, preferably 0.1 to 5 parts, more preferably 0.1 to 3 parts, further preferably 0.1 to 2 parts, per 100 parts of the base resin. More than 5 parts of the compound can reduce the resolution of the resist composition.

The resist composition of the invention may additionally include an acetylene alcohol derivative for the purpose of enhancing the shelf stability. Preferred acetylene alcohol derivatives are those having the general formula (Si) or (S2) below.

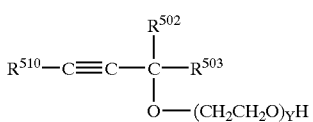

-continued

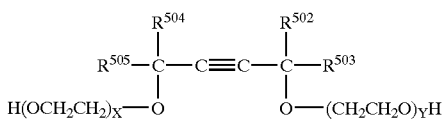

S2

In the formulas, $R^{501}$, $R^{502}$, $R^{503}$ $R^{504}$ and $R^{505}$ are each hydrogen or a straight, branched, or cyclic alkyl of 1 to 8 carbon atoms; and X and Y are each 0 or a positive number, satisfying $0 \leqq X \leqq 30$, $0 \leqq Y \leqq 30$, and $0 \leqq X+Y \leqq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industry K.K.

The acetylene alcohol derivative is preferably added in an amount of 0.01 to 2% by weight, and more preferably 0.02 to 1% by weight, per 100% by weight of the resist composition. Less than 0.01% by weight would be ineffective for improving coating characteristics and shelf stability, whereas more than 2% by weight would result in a resist having a low resolution.

The resist composition of the invention may include, as an optional ingredient, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Florade FC-430 and FC-431 from Sumitomo 3M Co., Ltd., Surflon S-141 and S-145 from Asahi Glass Co., Ltd., Unidyne DS-401, DS-403 and DS-451 from Daikin Industries Ltd., Megaface F-8151 from Dai-Nippon Ink & Chemicals Inc., and X-70-092 and X-70-093 from Shin-Etsu Chemical Co., Ltd. Preferred surfactants are Florade FC-430 from Sumitomo 3M and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.2 to 2.0 μm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV rays, excimer laser beams or x-rays in a dose of about 1 to 200 mJ/cm², and preferably about 5 to 100 mJ/cm², then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 248 to 193 nm, excimer laser beams, x-rays, or electron beams. The desired pattern may not be obtainable outside the upper and lower limits of the above range.

The resist composition comprising the polymer as a base resin lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser, a finely defined pattern having sidewalls perpendicular to the substrate can easily be formed.

EXAMPLE

Synthesis Examples and Examples are given below by way of illustration and not by way of limitation. The abbreviation GPC is gel permeation chromatography, SEM is scanning electron microscope, and TMAH is tetramethylammonium hydroxide.

Synthesis Example 1

Synthesis of (1,3-dioxolan-4-yl)methyl 5-norbornene-2-carboxylate (Monomer 1) (inclusive of a 6-membered ring acetal: 1,3-dioxan-5-yl 5-norbornene-2-carboxylate)

To a mixture of 104 g of glycerol formal, 111 g of triethylamine and 300 ml of toluene, 157 g of 5-norbornene-2-carbonyl chloride was added over one hour at 20° C. After 5 hours of stirring, 200 ml of water was added to stop the reaction and the mixture was allowed to separate. The organic layer was washed with water and saturated sodium chloride water, dried over anhydrous sodium sulfate, and concentrated in vacuum. It was further purified by vacuum distillation, obtaining 213 g of a mixture of (1,3-dioxolan-4-yl)methyl 5-norbornene-2-carboxylate and 1,3-dioxan-5-yl 5-norbornene-2-carboxylate (boiling point 111–115° C./530 Pa, yield 95%).

IR (thin film): ν=3138, 3061, 2976, 2866, 2777, 1732, 1570, 1446, 1335, 1273, 1232, 1225, 1174, 1155, 1095, 1066, 1045, 1022, 977, 943, 923, 715 cm$^{-1}$ $^1$H-NMR of (1,3-dioxolan-4-yl)methyl 5-norbornene-2-carboxylate (exo form/endo form=2/8) (300 MHz in CDCl$_3$): δ=1.20–1.55 (3H, m), 1.85–2.00 (1H, m), 2.27 (0.2H, m), 2.85–3.10 (2H, m), 3.20 (0.8H, m), 3.60–3.70 (1H, m), 3.80–4.30 (4H, m), 4.90 (1H, s), 5.02 (0.2H, s), 5.03 (0.8H, s), 5.90–5.95 (0.8H, m), 6.05–6.15 (0.4H, m), 6.15–6.25 (0.8H, m) $^1$H-NMR of 1,3-dioxan-5-yl 5-norbornene-2-carboxylate (exo form/endo form=2/8) (300 MHz in CDCl$_3$): δ=1.20–1.55 (3H, m), 1.85–2.00 (1H, m), 2.27 (0.2H, m), 2.85–3.10 (2H, m), 3.20 (0.8H, m), 3.80–4.20 (4H, m), 4.65 (0.8H, qui, J=3.4 Hz), 4.73 (0.2H, qui, J=3.2 Hz), 4.79 (0.8H, d, J=6.3 Hz), 4.80 (0.2H, d, J=6.3 Hz), 4.92 (0.8H, d, J=6.3 Hz), 4.94 (0.2H, d, J=6.3 Hz), 5.90–5.95 (0.8H, m), 6.05–6.15 (0.4H, m), 6.15–6.25 (0.8H, m)

Synthesis Example 2

Alternative synthesis of (1,3-dioxolan-4-yl)methyl 5-norbornene-2-carboxylate (Monomer 1) (inclusive of a 6-membered ring acetal: 1,3-dioxan-5-yl 5-norbornene-2-carboxylate)

A mixture of 104 g of glycerol formal, 152 g of methyl 5-norbornene-2-carboxylate, 2.0 g of sodium methoxide and 300 ml of toluene was heated under reflux for 5 hours while gradually distilling off methanol formed during the reaction. After cooling, the reaction solution was washed with satu rated sodium bicarbonate water, dried over anhydrous sodium sulfate, and concentrated in vacuum. It was further purified by vacuum distillation, obtaining 209 g of a mixture of (1,3-dioxolan-4-yl)methyl 5-norbornene-2-carboxylate and 1,3-dioxan-5-yl 5-norbornene-2-carboxylate (boiling point 111–115° C./530 Pa, yield 93%).

IR (thin film): ν=3138, 3061, 2976, 2866, 2777, 1732, 1570, 1446, 1335, 1273, 1232, 1225, 1174, 1155, 1095, 1066, 1045, 1022, 977, 943, 923, 715 cm$^{-1}$ $^1$H-NMR of (1,3-dioxolan-4-yl)methyl 5-norbornene-2-carboxylate (exo form/endo form=53/47) (300 MHz in CDCl$_3$): δ=1.20–1.55 (3H, m), 1.85–2.00 (1H, m), 2.27 (0.53H, m), 2.85–3.10 (2H, m), 3.20 (0.47H, m), 3.60–3.70 (1H, m), 3.80–4.30 (4H, m), 4.90 (1H, s), 5.02 (0.53H, s), 5.03 (0.47H, s), 5.90–5.95 (0.47H, m), 6.05–6.15 (1.06H, m), 6.15–6.25 (0.47H, m) $^1$H-NMR of 1,3-dioxan-5-yl 5-norbornene-2-carboxylate (exo form/endo form=53/47) (300 MHz in CDCl$_3$): δ=1.20–1.55 (3H, m), 1.85–2.00 (1H, m), 2.27 (0.53H, m), 2.85–3.10 (2H, m), 3.20 (0.47H, m), 3.80–4.20 (4H, m), 4.65 (0.47H, qui, J=3.4 Hz), 4.73 (0.53H, qui, J=3.2 Hz), 4.79 (0.47H, d, J=6.3 Hz), 4.80 (0.53H, d, J=6.3 Hz), 4.92 (0.47H, d, J=6.3 Hz), 4.94 (0.53H, d, J=6.3 Hz), 5.90–5.95 (0.47H, m), 6.05–6.15 (1.06H, m), 6.15–6.25 (0.47H, m)

Synthesis Example 3

Synthesis of (1,3-dioxolan-4-yl)methyl 5-(5-norbornen-2-yl)valerate (Monomer 2) (inclusive of a 6-membered ring acetal: 1,3-dioxan-5-yl 5-(5-norbornen-2-yl)valerate)

By following the procedure of Synthesis Example 1 except that 5-(5-norbornen-2-yl)valeric acid chloride was used instead of the 5-norbornene-2-carbonyl chloride, a mixture of (1,3-dioxolan-4-yl)methyl 5-(5-norbornen-2-yl)valerate and 1,3-dioxan-5-yl 5-(5-norbornen-2-yl)valerate was synthesized (boiling point 115–122° C./16 Pa, yield 90%).

IR (thin film): ν=3136, 3057, 2962, 2935, 2864, 2775, 1738, 1570, 1446, 1367, 1336, 1309, 1282, 1225, 1178, 1155, 1093, 1066, 1022, 980, 943, 719 cm$^{-1}$ $^1$H-NMR of (1,3-dioxolan-4-yl)methyl 5-(5-norbornen-2-yl)valerate main isomer (endo form) (300 MHz in CDCl$_3$): δ=0.46 (1H, ddd, J=11.2, 4.2, 2.5 Hz), 1.00–1.40 (6H, m), 1.50–1.70 (2H, m), 1.81 (1H, ddd, J=11.2, 9.1, 3.8 Hz), 1.95 (1H, m), 2.30–2.40 (2H, m), 2.70–2.80 (2H, m), 3.66 (1H, dd, J=8.1, 5.7 Hz), 3.97 (1H, t, J=8.1 Hz), 4.10 (1H, dd, J=11.6, 6.2 Hz), 4.15 (1H, dd, J=11.6, 4.4 Hz), 4.26 (1H, dddd, J=8.1, 6.2, 5.7, 4.4 Hz), 4.80 (1H, s), 5.02 (1H, s), 5.85–5.90 (1H, m), 6.05–6.10 (1H, m) $^1$H-NMR of 1,3-dioxan-5-yl 5-(5-norbornen-2-yl)valerate main isomer (endo form) (300 MHz in CDCl$_3$): δ=0.46 (1H, ddd, J=11.2, 4.2, 2.5 Hz), 1.00–1.40 (6H, m), 1.50–1.70 (2H, m), 1.81 (1H, ddd, J=11.2, 9.1, 3.8 Hz), 1.95 (1H, m), 2.30–2.40 (2H, m), 2.70–2.80 (2H, m), 3.90 (2H, dd, J=11.8, 3.6 Hz), 3.99.(2H, dd, J=11.8, 2.7 Hz), 4.72 (1H, tt, J=3.6, 2.7 Hz), 4.79 (1H, d, J=6.3 Hz), 4.93 (1H, d, J=6.3 Hz), 5.85–5.90 (1H, m), 6.05–6.10 (1H, m)

Synthesis Example 4

Alternative synthesis of (1,3-dioxolan-4-yl)methyl 5-(5-norbornen-2-yl)valerate (Monomer 2) (inclusive of a 6-membered ring acetal: 1,3-dioxan-5-yl 5-(5-norbornen-2-yl)valerate)

By following the procedure of Synthesis Example 2 except that methyl 5-(5-norbornen-2-yl)valerate was used instead of the methyl 5-norbornene-2-carboxylate, a mixture of (1,3-dioxolan-4-yl)methyl 5-(5-norbornen-2-yl)valerate and 1,3-dioxan-5-yl 5-(5-norbornen-2-yl)valerate was synthesized (yield 89%). The physical data of this product were coincident with those of Synthesis Example 3.

Monomer 1

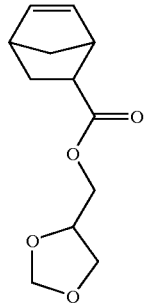

Monomer 2

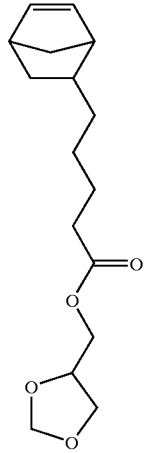

It was found from the data of $^1$H-NMR that the proportion of compound (i) and compound (v) in the mixtures obtained in the foregoing Synthesis Examples was about 1:1 in molar ratio.

Polymers within the scope of the invention were synthesized by the following procedure.

Synthesis Example 5

Synthesis of Polymer 1

In 150 ml of tetrahydrofuran were dissolved 56.1 g of a mixture of (1,3-dioxolan-4-yl)methyl 5-norbornene-2-carboxylate and 1,3-dioxan-5-yl 5-norbornene-2-carboxylate in a molar ratio of approximately 1:1, 65.0 g of 2-ethyl-2-norbornyl 5-norbornene-2-carboxylate and 24.5 g of maleic anhydride. To the solution was added 1.8 g of 2,2'-azobisisobutyronitrile. The solution was stirred for 15 hours at 60° C. and then concentrated in vacuum. The residue was dissolved in 400 ml of tetrahydrofuran, which was added dropwise to 10 liters of n-hexane. The resulting solids were collected by filtration, washed with 10 liters of n-hexane, and vacuum dried for 6 hours at 40° C. There was obtained 89.2 g of a polymer designated Polymer 1 whose structure is shown below. The yield was 61.3%.

The polymer was analyzed by GPC, finding a weight average molecular weight Mw of 9,100 based on a polystyrene standard, and a polydispersity index (Mw/Mn) of 1.84.

Synthesis Examples 6 to 16

Synthesis of Polymers 2 to 12

Polymers 2 to 12 were synthesized by the same procedure as above or a well-known procedure.

(Polymer 1)
x = 0.25, y = 0.25, z = 0.50
Mw = 9100, Mw/Mn = 1.84
(x = x1 + x2, x1:x2 ≈ 1:1)
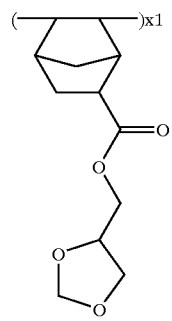 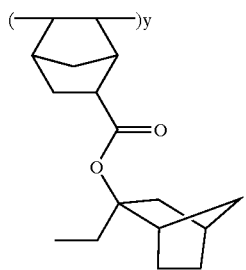 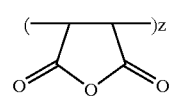 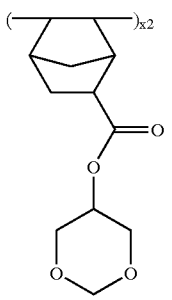
(Polymer 2)
x = 0.25, y = 0.25, z = 0.50
Mw = 8900, Mw/Mn = 1.79
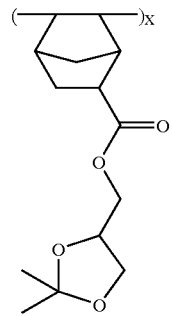 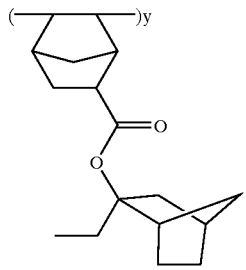 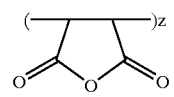
(Polymer 3)
x = 0.25, y = 0.25, z = 0.50
Mw = 9500, Mw/Mn = 1.88
(x = x1 + x2, x1:x2 ≈ 1:1)
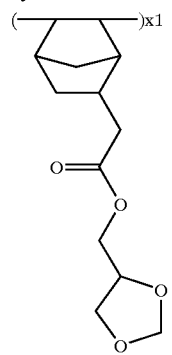 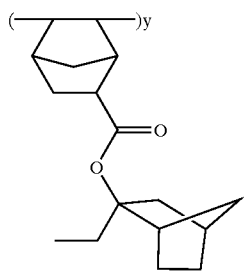 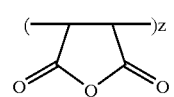 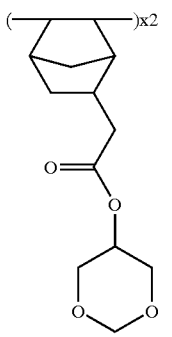
(Polymer 4)
x = 0.25, y = 0.25, z = 0.50
Mw = 9400, Mw/Mn = 1.85
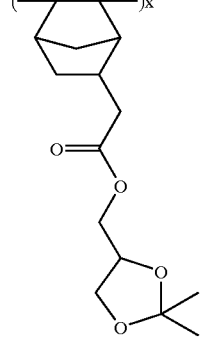 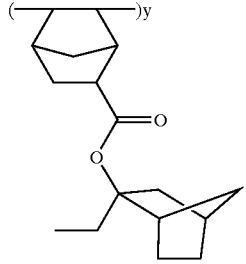 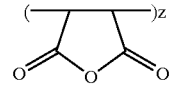
(Polymer 5)
x = 0.25, y = 0.25, z = 0.50
Mw = 6800, Mw/Mn = 1.67
(x = x1 + x2, x1:x2 ≈ 1:1
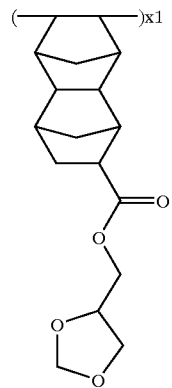 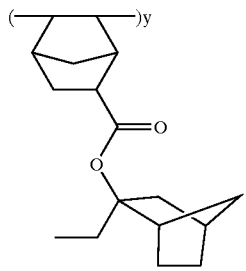 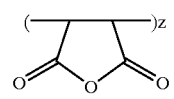 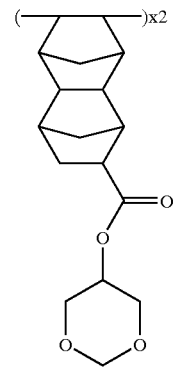

-continued
(Polymer 6)
x = 0.25, y = 0.25, z = 0.50
Mw = 8400, Mw/Mn = 1.80
(x = x1 + x2, x1:x2 ≈ 1:1)
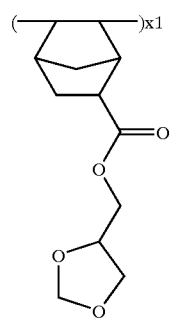 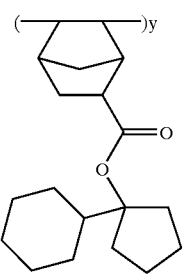 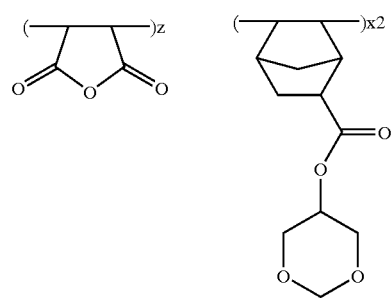
(Polymer 7)
x = 0.25, y = 0.25, z = 0.50
Mw = 9700, Mw/Mn = 1.76
(x = x1 + x2, x1:x2 ≈ 1:1)
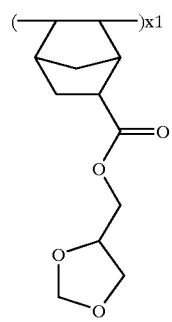 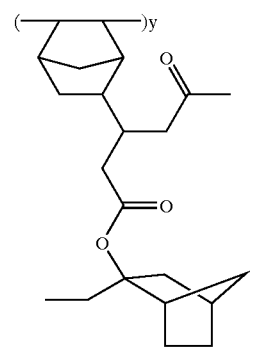 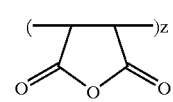 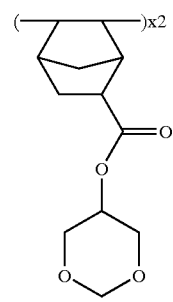
(Polymer 8)
x = 0.50, y = 0.50
Mw = 21600, Mw/Mn = 2.01
(x = x1 + x2, x1:x2 ≈ 1:1)
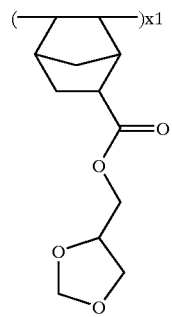 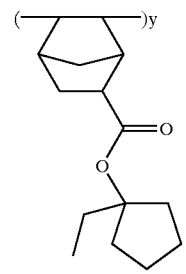 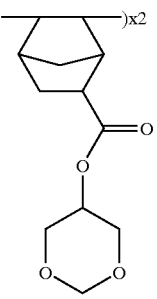
(Polymer 9)
x = 0.50, y = 0.50
Mw = 24000, Mw/Mn = 2.11
(x = x1 + x2, x1:x2 ≈ 1:1)
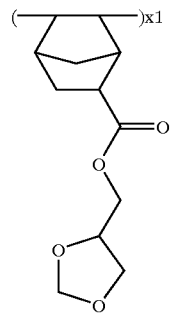 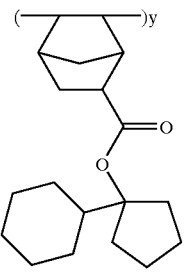 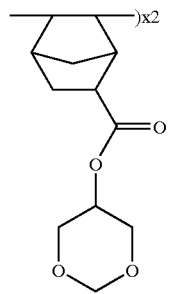

-continued (Polymer 10)
x = 0.30, y = 0.40, z = 0.30
Mw = 13300, Mw/Mn = 2.16
(x = x1 + x2, x1:x2 ≈ 1:1)

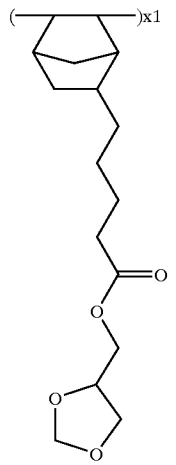 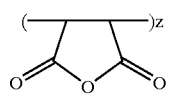 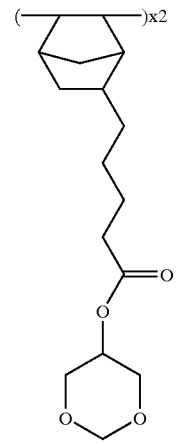

(Polymer 11)
x = 0.30, y = 0.40, z = 0.30
Mw = 11100, Mw/Mn = 2.06
(x = x1 + x2, x1:x2 ≈ 1:1)

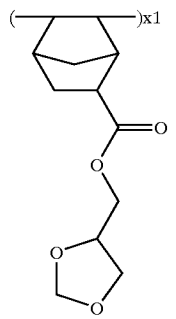 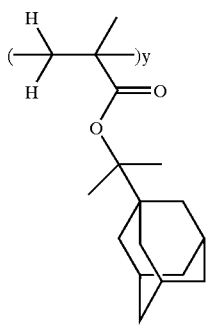 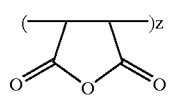 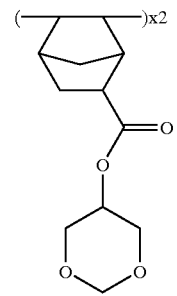

(Polymer 12)
x = 0.50, y = 0.50
Mw = 21600, Mw/Mn = 1.53
(x = x1 + x2, x1:x2 ≈ 1:1)

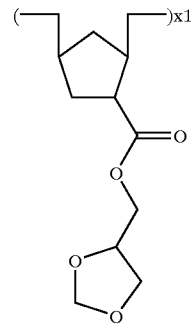 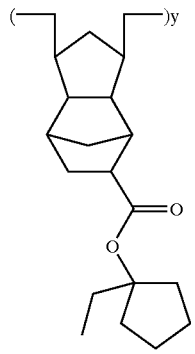 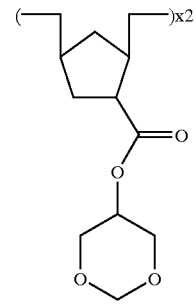

Example I

Resist compositions were formulated using inventive polymers as the base resin and examined for substrate adhesion.

Examples I-1 to I-5 and Comparative Examples 1, 2

Resist compositions were prepared by using inventive polymers (Polymers 1 to 5) or comparative polymers (Polymers 13 and 14 identified below) as the base resin, and dissolving the polymer, a photoacid generator (designated as PAG1), and a basic compound in a solvent in accordance with the formulation shown in Table 1. These compositions were each filtered through a Teflon® filter (pore diameter 0.2 μm), thereby giving resist solutions.

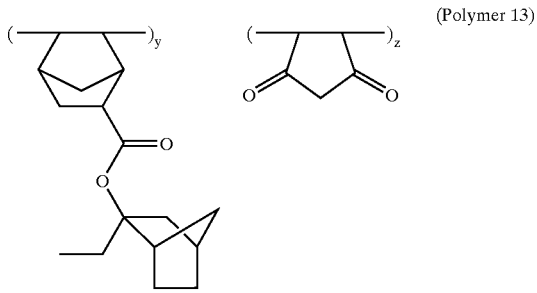

(Polymer 13)

y = 0.05, z = 0.50
Mw= 8800, Mw/Mn = 1.80

-continued (Polymer 14)

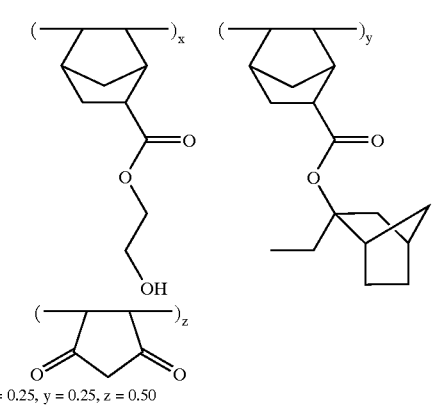

x = 0.25, y = 0.25, z = 0.50
Mw = 9700, Mw/Mn = 1.88

(PAG 1)

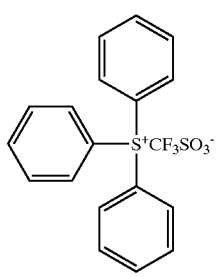

These resist solutions were spin coated onto hexamethyldisilazane-spray coated silicon wafers at 90° C. for 40 seconds, then heat treated at 110° C. for 90 seconds to give resist films having a thickness of 0.5 μm. The resist films were exposed using an KrF excimer laser stepper (Nikon Corporation; NA 0.5), then heat treated at 110° C. for 90 seconds, and puddle developed with a solution of 2.38% TMAH in water for 60 seconds, thereby giving 1:1 line-and-space patterns. The wafers as developed were observed under overhead SEM. The minimum width (μm) of lines left unstripped is the limit of adhesion of the resist under test.

The composition and test results of the resist materials are shown in Table 1.

The solvents and basic compound used are propylene glycol methyl ether acetate (PGMEA) and tributyl amine (TBA), respectively. It is noted that the solvent contained 0.01% by weight of surfactant Florade FC-430 (Sumitomo 3M).

TABLE 1

| | Resin (pbw) | Photoacid generator (pbw) | Basic compound (pbw) | Solvent (pbw) | Limit of adhesion (μm) |
|---|---|---|---|---|---|
| Example | | | | | |
| I-1 | Polymer 1 (80) | PAG 1 (1) | TBA (0.078) | PGMEA (480) | 0.22 |
| I-2 | Polymer 2 (80) | PAG 1 (1) | TBA (0.078) | PGMEA (480) | 0.24 |
| I-3 | Polymer 3 (80) | PAG 1 (1) | TBA (0.078) | PGMEA (480) | 0.22 |
| I-4 | Polymer 4 (80) | PAG 1 (1) | TBA (0.078) | PGMEA (480) | 0.26 |

TABLE 1-continued

| | Resin (pbw) | Photoacid generator (pbw) | Basic compound (pbw) | Solvent (pbw) | Limit of adhesion (μm) |
|---|---|---|---|---|---|
| I-5 | Polymer 5 (80) | PAG 1 (1) | TBA (0.078) | PGMEA (480) | 0.28 |
| Comparative Example | | | | | |
| 1 | Polymer 13 (80) | PAG 1 (1) | TBA (0.078) | PGMEA (480) | >0.50 |
| 2 | Polymer 14 (80) | PAG 1 (1) | TBA (0.078) | PGMEA (480) | >0.50 |

It is evident from Table 1 that the polymers within the scope of the invention have good substrate adhesion.

Example II

Resist compositions were formulated using inventive polymers and examined for resolution upon KrF excimer laser exposure.

Examples II-1 to II-21: Evaluation of Resist Resolution

Resist compositions were prepared by using Polymers 1 to 12 as the base resin, and dissolving the polymer, a photoacid generator (designated as PAG1 and 2), a dissolution regulator (designated as DRR1 to 4), a basic compound, and a compound having a ≡C—COOH group in the molecule (ACC1 and 2) in a solvent in accordance with the formulation shown in Table 2. These compositions were each filtered through a Teflon filter (pore diameter 0.2 μm), thereby giving resist solutions.

(PAG 1)

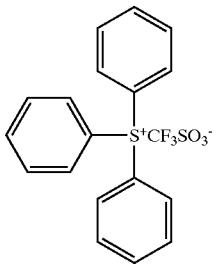

(PAG 2)

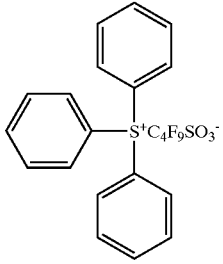

(DDR 1)

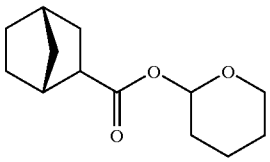

(DDR 2)

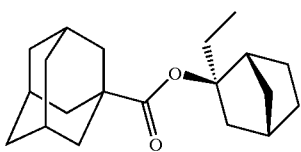

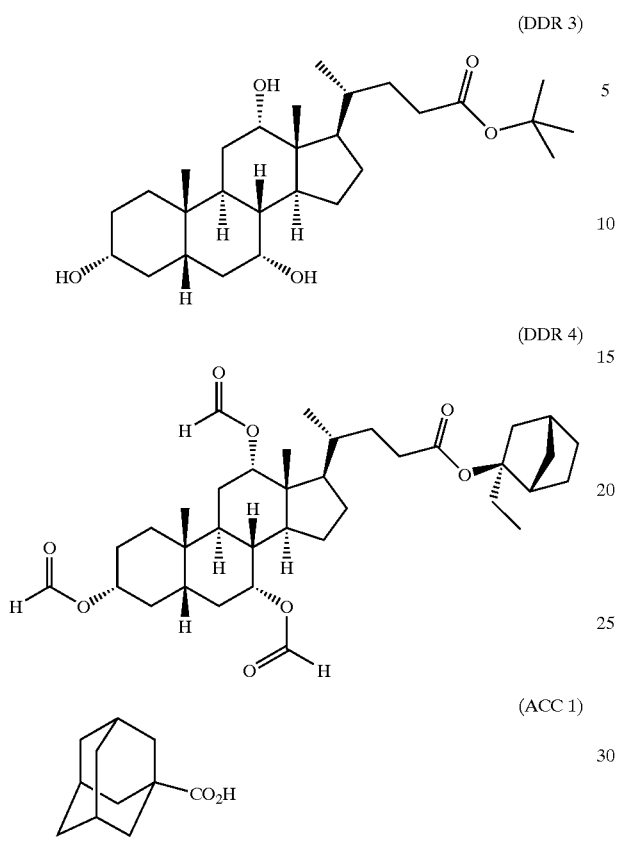

(DDR 3)

(DDR 4)

(ACC 1)

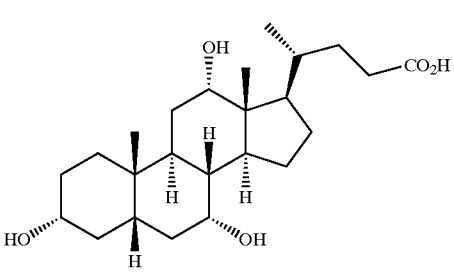

(ACC 2)

The solvent and basic compounds used are as follows. It is noted that the solvent contained 0.01% by weight of surfactant Florade FC-430 (Sumitomo 3M).
PGMEA: propylene glycol methyl ether acetate
TEA: triethanolamine
TMMEA: trismethoxymethoxyethylamine
TMEMEA: trismethoxyethoxymethoxyethylamine These resist solutions were spin coated onto hexamethyldisilazane-spray coated silicon wafers at 90° C. for 90 seconds, then heat treated at 110° C. for 90 seconds to give resist films having a thickness of 0.5 μm. The resist films were exposed using an KrF excimer laser stepper (Nikon Corporation; NA 0.5), then heat treated at 110° C. for 90 seconds, and puddle developed with a solution of 2.38% TMAH in water for 60 seconds, thereby giving 1:1 line-and-space patterns.

The wafers as developed were sectioned and observed under sectional SEM. The optimal dose (Eop, mJ/cm$^2$) was defined as the dose which provided a 1:1 resolution at the top and bottom of a 0.30 μm line-and-space pattern. The resolution of the resist under evaluation was defined as the minimum line width (μm) of the lines and spaces that separated at the optimal dose. The shape of the resolved resist pattern was examined under a SEM.

The composition and test results of the resist materials are shown in Table 2.

TABLE 2

| Example | Resin (pbw) | Photoacid generator (pbw) | Dissolution regulator (pbw) | Basic compound (pbw) | Solvent (pbw) | Eop (mJ/cm$^2$) | Resolution (μm) | Shape |
|---|---|---|---|---|---|---|---|---|
| II-1 | Polymer 1 (80) | PAG 1 (1) | — | TEA (0.063) | PGMEA (480) | 26.0 | 0.20 | rectangular |
| II-2 | Polymer 2 (80) | PAG 1 (1) | — | TEA (0.063) | PGMEA (480) | 26.0 | 0.20 | rectangular |
| II-3 | Polymer 3 (80) | PAG 1 (1) | — | TEA (0.063) | PGMEA (480) | 25.0 | 0.20 | rectangular |
| II-4 | Polymer 4 (80) | PAG 1 (1) | — | TEA (0.063) | PGMEA (480) | 26.0 | 0.20 | rectangular |
| II-5 | Polymer 5 (80) | PAG 1 (1) | — | TEA (0.063) | PGMEA (480) | 28.0 | 0.22 | rectangular |
| II-6 | Polymer 6 (80) | PAG 1 (1) | — | TEA (0.063) | PGMEA (480) | 22.0 | 0.20 | rectangular |
| II-7 | Polymer 7 (80) | PAG 1 (1) | — | TEA (0.063) | PGMEA (480) | 21.0 | 0.20 | rectangular |
| II-8 | Polymer 8 (80) | PAG 1 (1) | — | TEA (0.063) | PGMEA (480) | 26.0 | 0.22 | rectangular |
| II-9 | Polymer 9 (80) | PAG 1 (1) | — | TEA (0.063) | PGMEA (480) | 20.0 | 0.20 | rectangular |
| II-10 | Polymer 10 (80) | PAG 1 (1) | — | TEA (0.063) | PGMEA (560) | 23.0 | 0.22 | rectangular |
| II-11 | Polymer 11 (80) | PAG 1 (1) | — | TEA (0.063) | PGMEA (560) | 24.0 | 0.22 | rectangular |
| II-12 | Polymer 12 (80) | PAG 1 (1) | — | TEA (0.063) | PGMEA (640) | 23.0 | 0.24 | rectangular |
| II-13 | Polymer 6 (80) | PAG 2 (1) | — | TEA (0.063) | PGMEA (480) | 25.0 | 0.20 | rectangular |
| II-14 | Polymer 6 (80) | PAG 2 (1) | — | TMMEA (0.118) | PGMEA (480) | 26.0 | 0.20 | rectangular |
| II-15 | Polymer 6 (80) | PAG 2 (1) | — | TMEMEA (0.173) | PGMEA (480) | 26.0 | 0.22 | rectangular |

TABLE 2-continued

| Example | Resin (pbw) | Photoacid generator (pbw) | Dissolution regulator (pbw) | Basic compound (pbw) | Solvent (pbw) | Eop (mJ/cm$^2$) | Resolution ($\mu$m) | Shape |
|---|---|---|---|---|---|---|---|---|
| II-16 | Polymer 7 (70) | PAG 2 (1) | DRR 1 (10) | TEA (0.063) | PGMEA (480) | 18.0 | 0.22 | rectangular |
| II-17 | Polymer 7 (70) | PAG 2 (1) | DRR 2 (10) | TEA (0.063) | PGMEA (480) | 19.0 | 0.22 | rectangular |
| II-18 | Polymer 7 (70) | PAG 2 (1) | DRR 3 (10) | TEA (0.063) | PGMEA (480) | 22.0 | 0.22 | rectangular |
| II-19 | Polymer 7 (70) | PAG 2 (1) | DRR 4 (10) | TEA (0.063) | PGMEA (480) | 20.0 | 0.20 | rectangular |
| II-20 | Polymer 7 (80) | PAG 2 (1) | ACC 1 (4) | TEA (0.063) | PGMEA (480) | 22.0 | 0.22 | rectangular |
| II-21 | Polymer 7 (80) | PAG 2 (1) | ACC 2 (4) | TEA (0.063) | PGMEA (480) | 23.0 | 0.22 | rectangular |

It is seen from Table 2 that the resist compositions within the scope of the invention have a high sensitivity and resolution upon KrF excimer laser exposure.

TABLE 3

| Example | Resin (pbw) | Photoacid generator (pbw) | Basic compound (pbw) | Solvent (pbw) | Eop (mJ/cm$^2$) | Resolution ($\mu$m) | Shape |
|---|---|---|---|---|---|---|---|
| III-1 | Polymer 1 (80) | PAG 1 (1) | TEA (0.063) | PGMEA (480) | 17.5 | 0.15 | rectangular |
| III-2 | Polymer 1 (80) | PAG 2 (1) | TMMEA (0.118) | PGMEA (480) | 18.0 | 0.15 | rectangular |

Example III

Resist compositions were formulated using inventive polymers and examined for resolution upon ArF excimer laser exposure.

Examples III-1 to III-2: Evaluation of Resist Resolution

Resist compositions were prepared as in Example II in accordance with the formulation shown in Table 3.

The resulting resist solutions were spin coated onto hexamethyldisilazane-spray coated silicon wafers at 90° C. for 90 seconds, then heat treated at 110° C. for 90 seconds to give resist films having a thickness of 0.5 $\mu$m. The resist films were exposed using an ArF excimer laser stepper (Nikon Corporation; NA 0.55), then heat treated at 110° C. for 90 seconds, and puddle developed with a solution of 2.38% TMAH in water for 60 seconds, thereby giving 1:1 line-and-space patterns.

The wafers as developed were sectioned and observed under sectional SEM. The optimal dose (Eop, mJ/cm$^2$) was D defined as the dose which provided a 1:1 resolution at the top and bottom of a 0.25 $\mu$m line-and-space pattern. The resolution of the resist under evaluation was defined as the minimum line width ($\mu$m) of the lines and spaces that separated at the optimal dose. The shape of the resolved resist pattern was examined under a SEM.

The composition and test results of the resist materials are shown in Table 3. It is noted that the solvents and basic compounds in Table 3 are as follows. It is noted that the solvent contained 0.01% by weight of surfactant Florade FC-430 (Sumitomo 3M).
PGMEA: propylene glycol methyl ether acetate
TEA: triethanolamine
TMMEA: trismethoxymethoxyethylamine It is seen from Table 3 that the resist compositions within the scope of the invention have a high sensitivity and resolution upon ArF excimer laser exposure.

Japanese Patent Application Nos. 2000-301933 and 2001-031720 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A cyclic acetal compound of the following general formula (i):

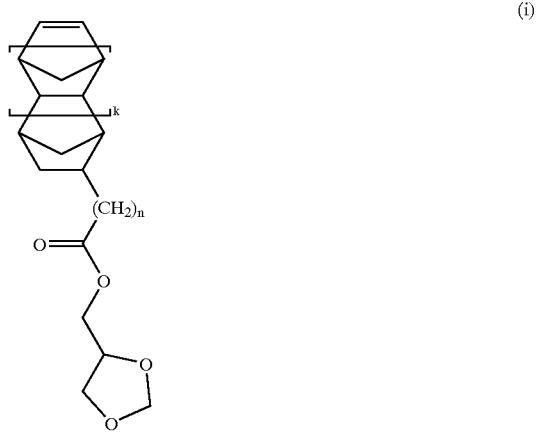

wherein k is 0 or 1 and n is an integer from 0 to 6.

2. The cyclic acetal compound of claim 1 having the following general formula (ii):

3. A cyclic acetal compound mixture comprising a 5-membered ring acetal compound of the general formula (i) and a 6-membered ring acetal compound of the general formula (v):

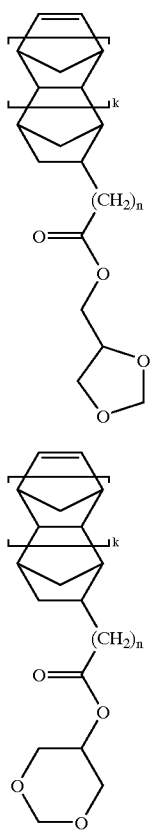

(i)

(v)

wherein k is 0 or 1 and n is an integer from 0 to 6.

4. The cyclic acetal compound mixture of claim 3 comprising a 5-membered ring acetal compound of the general formula (ii) and a 6-membered ring acetal compound of the general formula (vi):

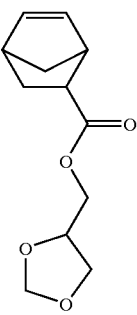

(ii)

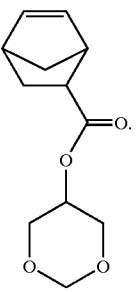

(vi)

5. The mixture of claim 3, wherein the molar ratio of the compound of general formula (i) to compound of general formula (v) is between 7:3 to 3:7.

* * * * *